(12) United States Patent
Beulke et al.

(10) Patent No.: US 8,152,832 B2
(45) Date of Patent: Apr. 10, 2012

(54) APPARATUS FOR ANCHORING AN INTRAVASCULAR DEVICE ALONG A GUIDEWIRE

(75) Inventors: Mel R. Beulke, Bloomington, MN (US); Thomas E. Broome, Shakopee, MN (US); Robert L. Cassell, Otsego, MN (US); John M. K. Daniel, Fremont, CA (US); Alan D. Eskuri, Hanover, MN (US); James G. Hansen, Coon Rapids, MN (US); Gary R. Kostur, Golden Valley, MN (US); Douglas B. Molland, Tonka Bay, MN (US); Scott R. Smith, Chaska, MN (US); Jeffrey H. Vogel, Brooklyn Park, MN (US); Anthony C. Vrba, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1186 days.

(21) Appl. No.: 11/621,921

(22) Filed: Jan. 10, 2007

(65) Prior Publication Data

US 2007/0123913 A1 May 31, 2007

Related U.S. Application Data

(63) Continuation of application No. 10/373,481, filed on Feb. 24, 2003, now abandoned.

(51) Int. Cl.
*A61M 29/00* (2006.01)
(52) U.S. Cl. ......... 606/200; 606/191; 606/194; 606/198
(58) Field of Classification Search ........................ None
See application file for complete search history.

(56) References Cited

U.S. PATENT DOCUMENTS

| | | | |
|---|---|---|---|
| 3,472,230 A | 10/1969 | Fogarty | |
| 3,952,747 A | 4/1976 | Kimmell, Jr. | |
| 3,996,938 A | 12/1976 | Clark, III | |
| 4,425,908 A | 1/1984 | Simon | |
| 4,643,184 A | 2/1987 | Mobin-Uddin | |
| 4,662,885 A | 5/1987 | DiPisa, Jr. | |
| 4,706,671 A | 11/1987 | Weinrib | |
| 4,723,549 A | 2/1988 | Wholey et al. | |
| 4,790,812 A | 12/1988 | Hawkins, Jr. et al. | |
| 4,790,813 A | 12/1988 | Kensey | |
| 4,794,928 A | 1/1989 | Kletschka | |
| 4,857,045 A | 8/1989 | Rydell | |
| 4,873,978 A | 10/1989 | Ginsburg | |

(Continued)

FOREIGN PATENT DOCUMENTS

WO 96/01591 A1 1/1996

*Primary Examiner* — Thomas J Sweet
*Assistant Examiner* — Kevin Everage
(74) *Attorney, Agent, or Firm* — Seager, Tufte & Wickhem LLC

(57) ABSTRACT

Anchoring mechanisms for releasably securing an intravascular device along an elongated member such as a guidewire or catheter. The anchoring mechanism may include an object that can be actuated between an unlocked position and a locked position. In the unlocked position, the anchoring mechanism is slidably and rotationally disposed about the elongated member. In the locked position, the anchoring mechanism is releasably secured to the elongated member, preventing movement thereon. A placement mechanism such as a tubular member can be utilized to actuate the anchoring mechanism between the unlocked and locked positions.

7 Claims, 24 Drawing Sheets

U.S. PATENT DOCUMENTS

| | | |
|---|---|---|
| 4,886,061 A | 12/1989 | Fischell et al. |
| 4,969,891 A | 11/1990 | Gewertz |
| 5,011,488 A | 4/1991 | Ginsburg |
| 5,071,407 A | 12/1991 | Termin et al. |
| 5,133,733 A | 7/1992 | Rasmussen et al. |
| 5,160,342 A | 11/1992 | Reger et al. |
| 5,192,286 A | 3/1993 | Phan et al. |
| 5,324,304 A | 6/1994 | Rasmussen |
| 5,329,942 A | 7/1994 | Gunther et al. |
| 5,370,657 A | 12/1994 | Irie |
| 5,415,630 A | 5/1995 | Gory et al. |
| 5,419,774 A | 5/1995 | Willard et al. |
| 5,462,529 A | 10/1995 | Simpson et al. |
| 5,536,242 A | 7/1996 | Willard et al. |
| 5,549,626 A | 8/1996 | Miller et al. |
| 5,662,671 A | 9/1997 | Barbut et al. |
| 5,669,933 A | 9/1997 | Simon et al. |
| 5,769,816 A | 6/1998 | Barbut et al. |
| 5,779,716 A | 7/1998 | Cano et al. |
| 5,800,457 A | 9/1998 | Gelbfish |
| 5,800,525 A | 9/1998 | Bachinski et al. |
| 5,807,398 A | 9/1998 | Shaknovich |
| 5,814,064 A | 9/1998 | Daniel et al. |
| 5,833,650 A | 11/1998 | Imran |
| 5,848,964 A | 12/1998 | Samuels |
| 5,911,734 A | 6/1999 | Tsugita et al. |
| 6,066,149 A | 5/2000 | Samon et al. |
| 6,066,158 A | 5/2000 | Engelson et al. |
| 6,142,987 A | 11/2000 | Tsugita |
| 6,152,946 A | 11/2000 | Broome et al. |
| 6,168,579 B1 | 1/2001 | Tsugita |
| 6,171,327 B1 | 1/2001 | Daniel et al. |
| 6,179,861 B1 | 1/2001 | Khosravi et al. |
| 6,203,561 B1 | 3/2001 | Ramee et al. |
| 6,206,868 B1 | 3/2001 | Parodi |
| 6,221,006 B1 | 4/2001 | Dubrul et al. |
| 6,277,139 B1 | 8/2001 | Levinson et al. |
| 6,605,102 B1 | 8/2003 | Mazzocchi et al. |
| 2001/0041908 A1 * | 11/2001 | Levinson et al. ............ 606/200 |

* cited by examiner

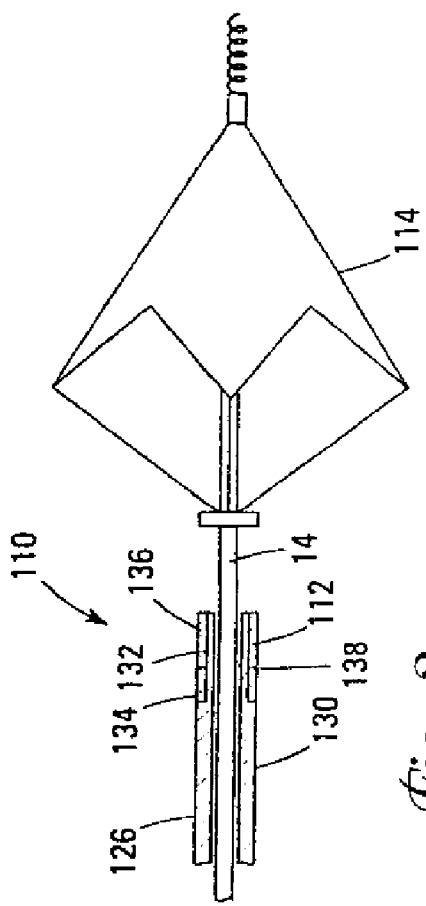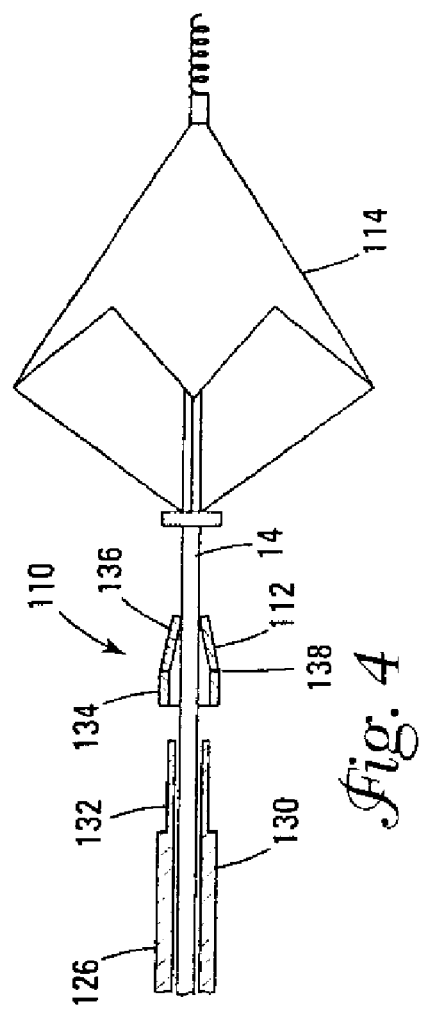

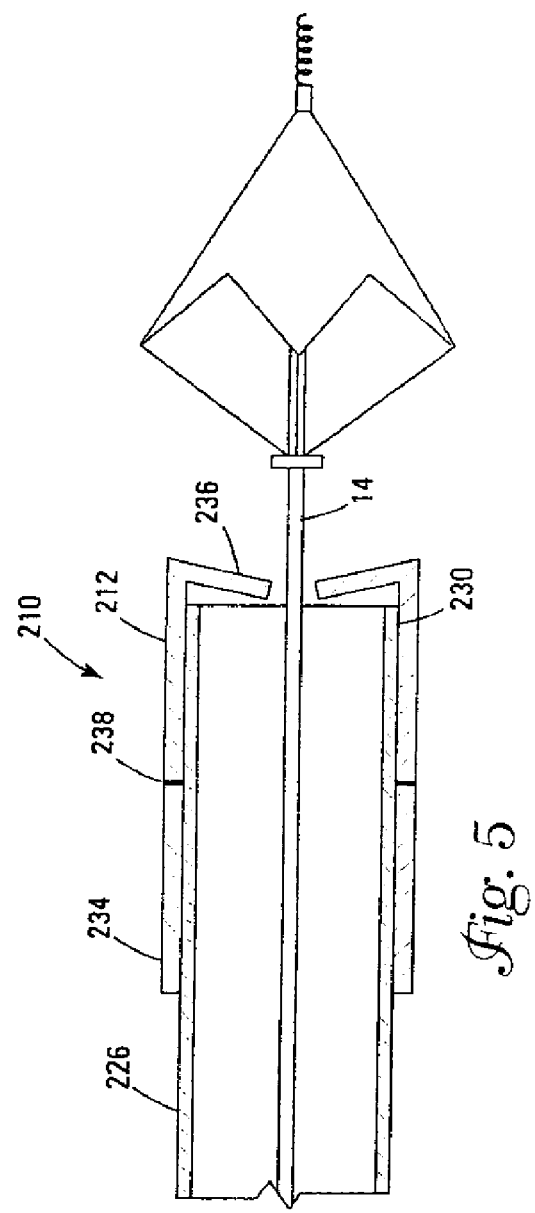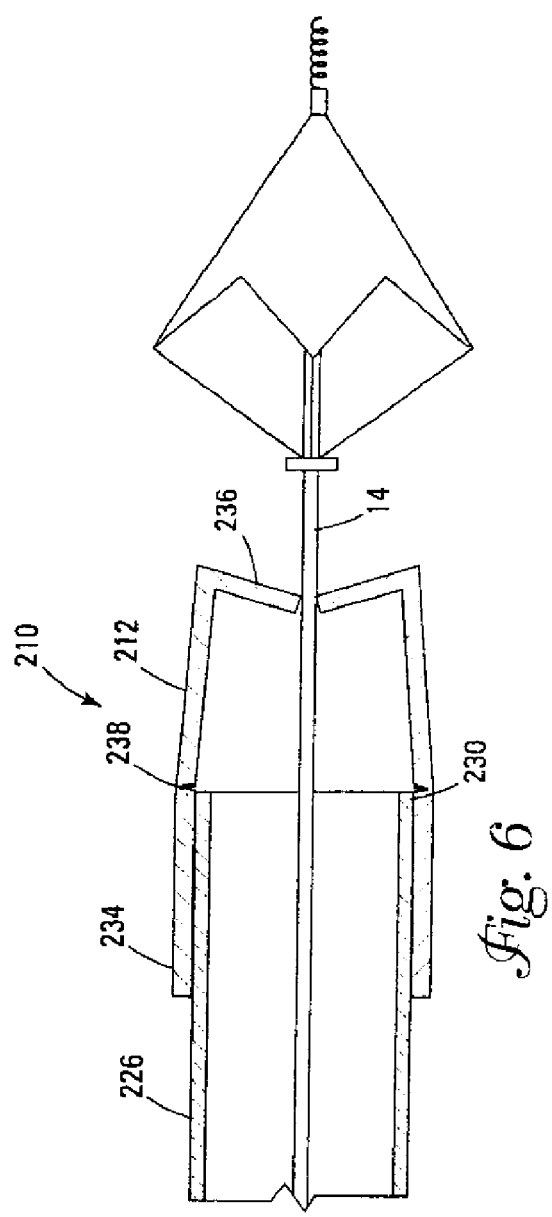

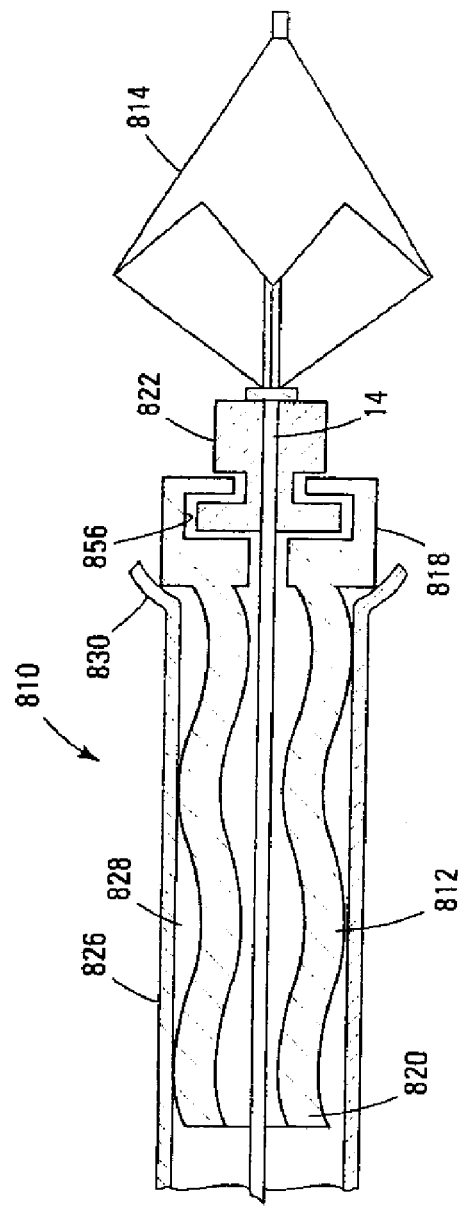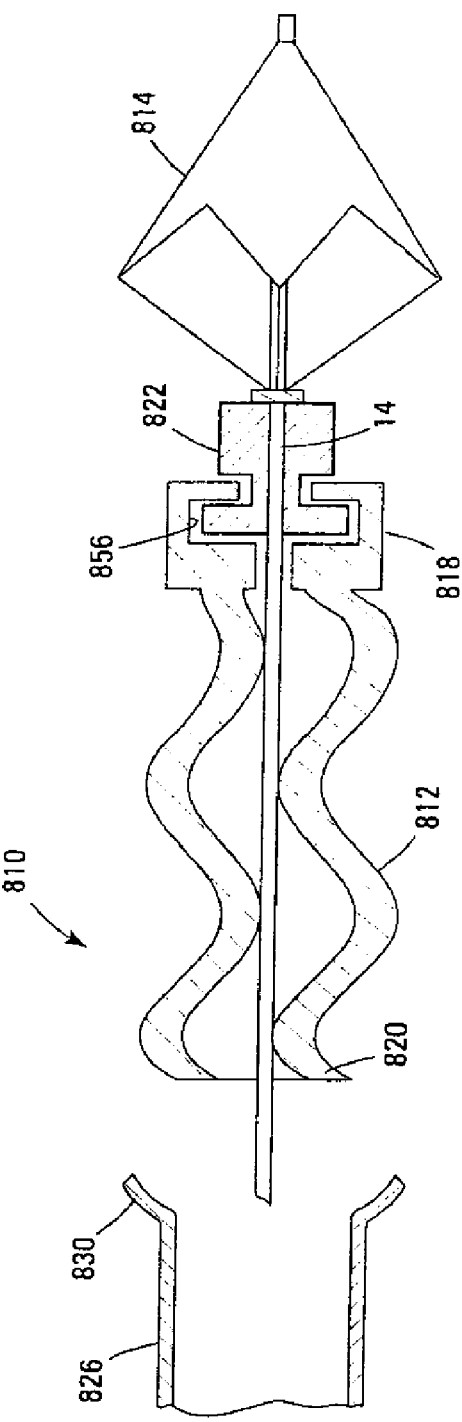
Fig. 18
Fig. 19

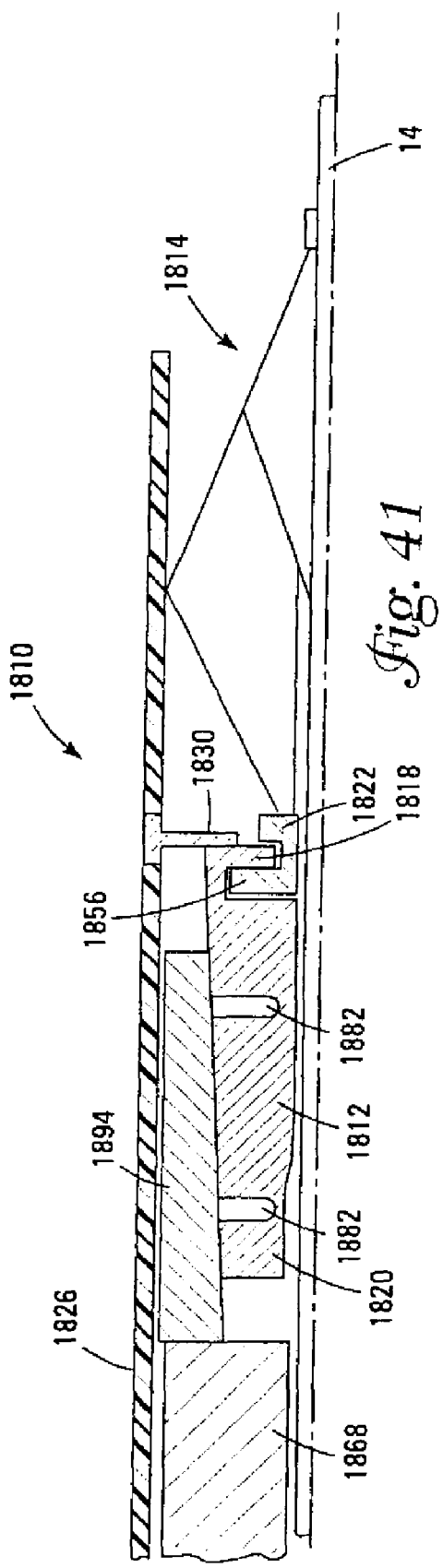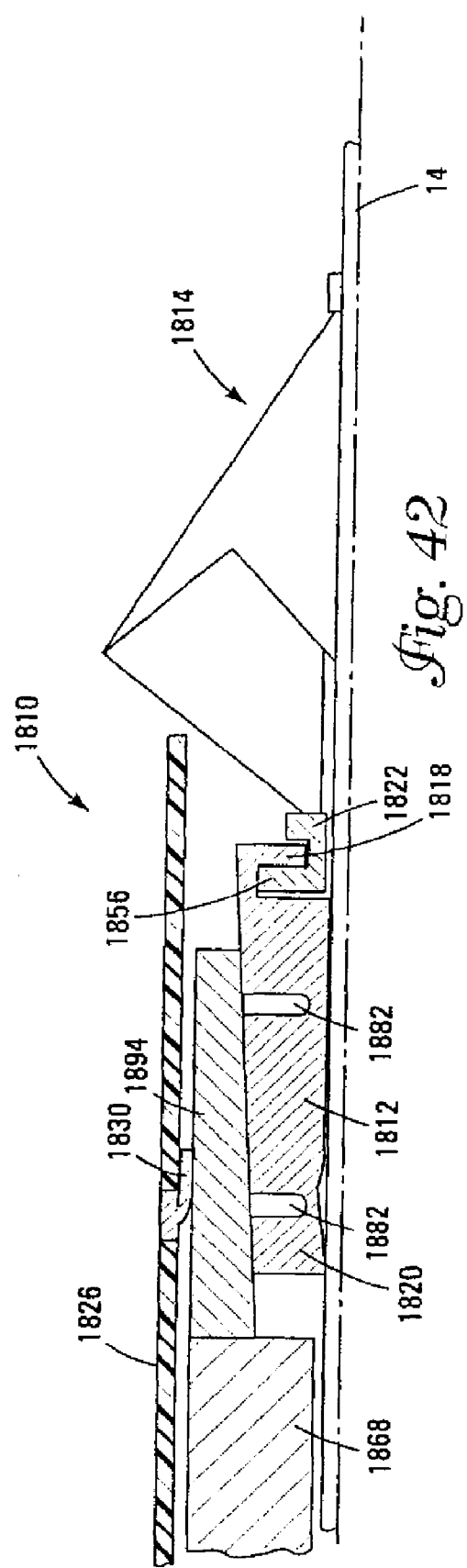

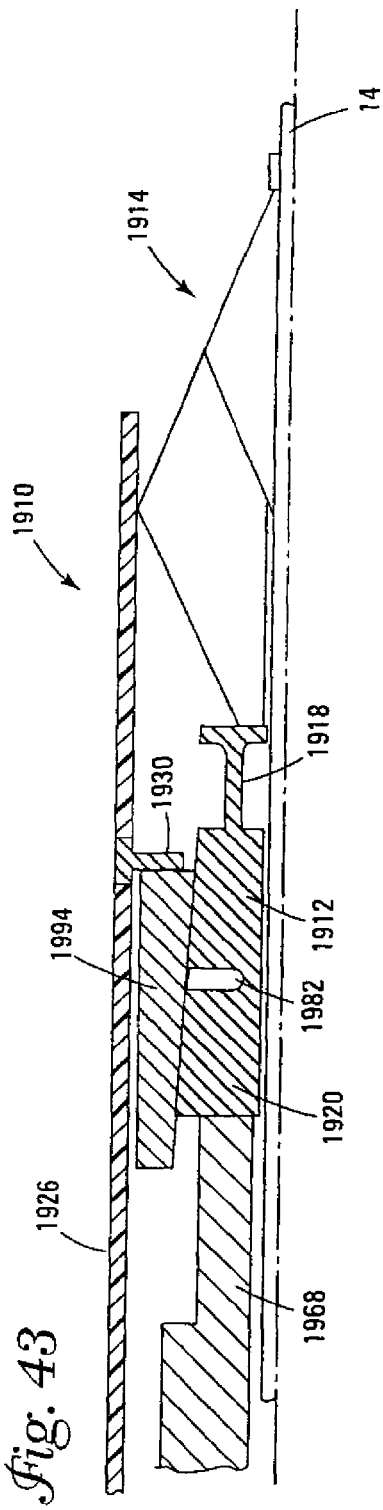
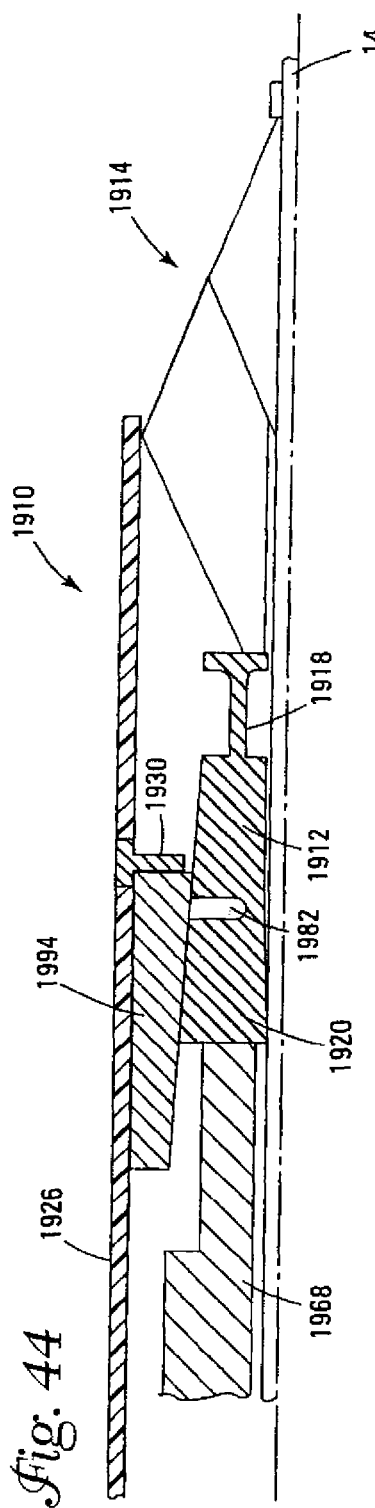
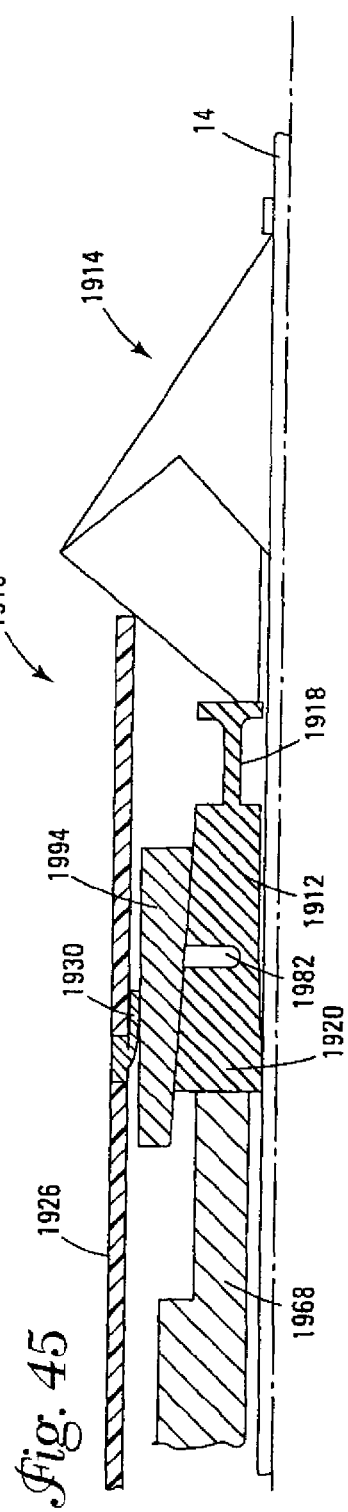

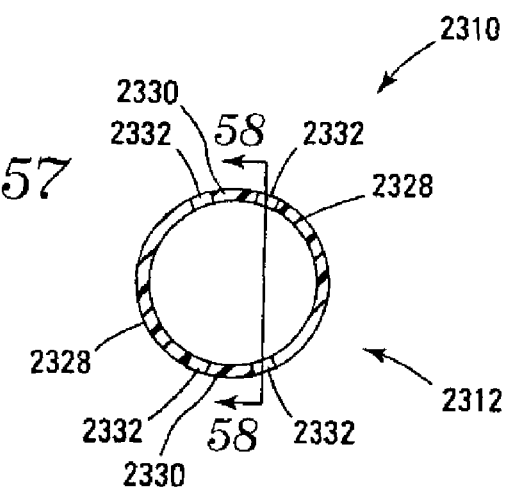
Fig. 57
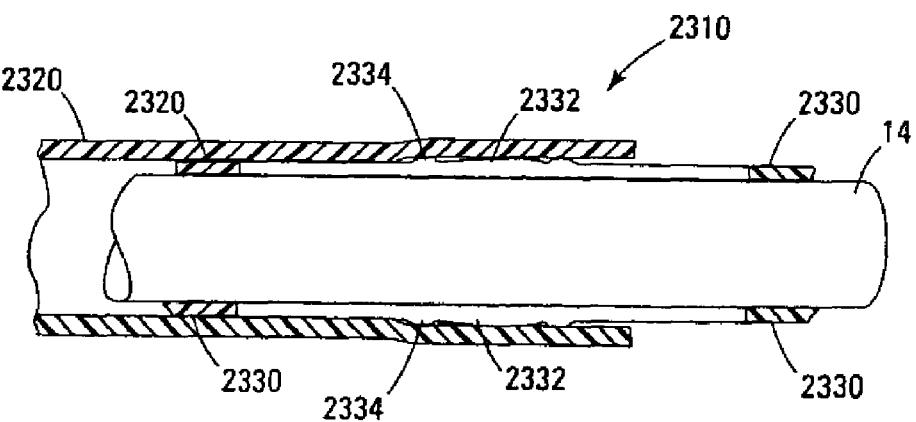
Fig. 58
Fig. 59

APPARATUS FOR ANCHORING AN INTRAVASCULAR DEVICE ALONG A GUIDEWIRE

This application is a continuation of U.S. application Ser. No. 10/373,481 filed Feb. 24, 2003.

FIELD OF THE INVENTION

The present invention pertains to anchoring mechanisms for intravascular devices. More specifically, the present invention relates to anchoring mechanisms for releasably securing an intravascular device to an elongated member disposed within a blood vessel.

BACKGROUND OF THE INVENTION

Medical procedures to treat occlusive vascular diseases, such as angioplasty, atherectomy and stent deployment, routinely involve the insertion and subsequent removal of various intravascular devices. In an angioplasty procedure, for example, a physician will typically advance a guidewire having an attached embolic protection filter to a desired location within the body, and subsequently deploy a balloon catheter to dislodge embolic debris or thrombus from a lesion. In some instances, the physician may wish to deploy more than one device during the procedure. For example, if the first embolic protection filter becomes occluded with debris dislodged during the angioplasty procedure, the physician may wish to replace the occluded filter with a second filter.

One limitation with the prior art is the inability to deploy more than one device along a single guidewire without having to remove the guidewire from the patient's body. Although more recent developments in the art have focused on the use of multiple wires to rapidly deploy and exchange such devices, techniques employing a single guidewire typically require the physician to remove the guidewire from the body prior to the insertion of another device.

SUMMARY OF THE INVENTION

The present invention pertains to anchoring mechanisms for intravascular devices. More specifically, the present invention relates to anchoring mechanisms for releasably securing an intravascular device to a guidewire disposed within the vasculature of a patient.

In one exemplary embodiment of the present invention, an anchoring mechanism for releasably securing an intravascular device to a guidewire comprises an embolic protection filter actuatable between an unlocked (i.e. disengaged) position and a locked (i.e. engaged) position. In the unlocked position, the anchoring mechanism is slidably and rotationally disposed along the guidewire, allowing the embolic protection filter to be advanced through the patient's vasculature. In the locked position, the anchoring mechanism is releasably secured to the guidewire, substantially preventing movement of the device along the guidewire. In certain implementations of the present invention, a placement device can be utilized to place the anchoring mechanism at a desired point along the guidewire. In other implementations, a retrieval mechanism can be utilized to disengage the anchoring mechanism from the guidewire.

BRIEF DESCRIPTION OF THE DRAWINGS

FIG. 3 is a cross-sectional view of an anchoring mechanism in accordance with another embodiment of the present invention, wherein the anchoring mechanism includes a split tube segment;

FIG. 4 is another cross-sectional view of the anchoring mechanism of FIG. 3, wherein the anchoring mechanism is releasably secured to the guidewire;

FIG. 5 is a cross-sectional view of an anchoring mechanism in accordance with another embodiment of the present invention, wherein the anchoring mechanism includes one or more leaf clamps;

FIG. 6 is another cross-sectional view of the anchoring mechanism of FIG. 5, wherein the anchoring mechanism is releasably secured to the guidewire;

FIG. 18 is a cross-sectional view of an anchoring mechanism in accordance with another embodiment of the present invention, wherein the anchoring mechanism includes a shape-memory tube;

FIG. 19 is another cross-sectional view of the anchoring mechanism of FIG. 18, wherein the anchoring mechanism is releasably secured to the guidewire;

FIG. 41 is a cross-sectional view of an anchoring mechanism in accordance with another embodiment of the present invention, wherein the anchoring mechanism includes a wedge;

FIG. 42 is another cross-sectional view of the anchoring mechanism of FIG. 41, wherein the anchoring mechanism is releasably secured to the guidewire;

FIG. 43 is a cross-sectional view of an anchoring mechanism in accordance with another embodiment of the present invention employing a wedge;

FIG. 44 is another cross-sectional view of the anchoring mechanism of FIG. 43, wherein the object is advanced along the wedge in a second position;

FIG. 45 is yet another cross-sectional view of the anchoring mechanism of FIG. 43, wherein anchoring mechanism is releasably secured to the guidewire in a third position;

FIG. 57 is a cross-sectional view of an anchoring mechanism in accordance with another embodiment of the present invention, wherein the anchoring mechanism includes a slotted tube having a wall with varying section moduli;

FIG. 58 is another cross-sectional view of the anchoring mechanism of FIG. 57 along line 58-58, wherein the anchoring mechanism is slidably disposed along the guidewire; and FIG. 59 is another cross-sectional view of the anchoring mechanism of FIG. 57, wherein the anchoring mechanism is releasably secured to the guidewire.

DETAILED DESCRIPTION OF THE INVENTION

Figure 1:
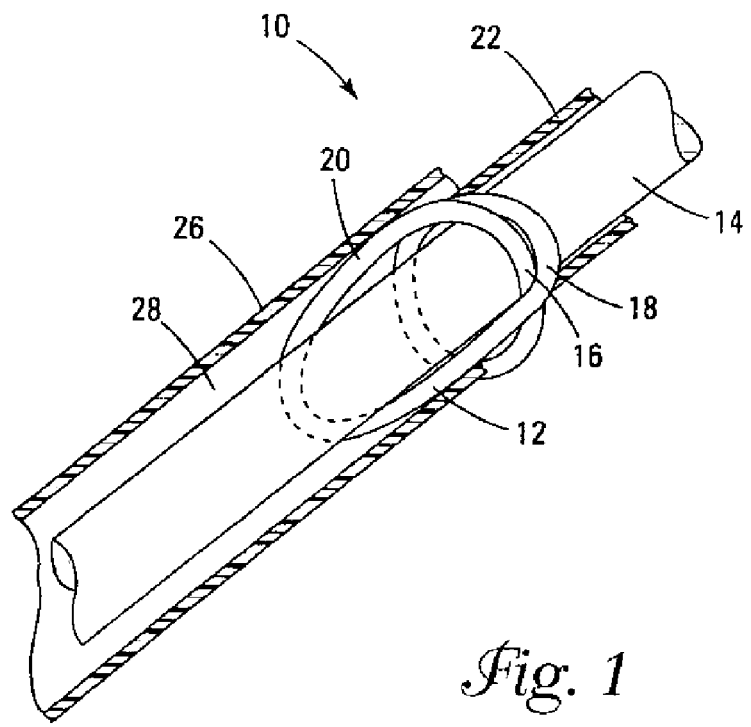
FIG. 1 is a cross-sectional view of an anchoring mechanism in accordance with an embodiment of the present invention, wherein the anchoring mechanism includes a spring coil.

The following description should be read with reference to the drawings wherein like reference numerals indicate like elements throughout the several views. The detailed description and drawings illustrate example embodiments of the claimed invention. The drawings, which are not necessarily to scale, depict several embodiments and are not intended to limit the scope of the invention. Although examples of construction, dimensions, materials and manufacturing processes are illustrated for the various elements, those skilled in the art will recognize that many of the examples provided have suitable alternatives that may be utilized.

FIG. 1 is a cross-sectional view illustrating an anchoring mechanism 10 in accordance with an exemplary embodiment of the present invention. Anchoring mechanism 10 comprises a spring coil 12 slidably and rotationally disposable about a guidewire 14 in an unlocked (i.e. disengaged) position, and releasably securable to the guidewire 14 in a locked (i.e. engaged) position.

Spring coil 12 comprises a wire coil segment 16 adapted to receive guidewire 14, a distal portion 18, and a proximal portion 20. The distal portion 18 of spring coil 12 is attached to a proximal end 22 of an intravascular device such as an embolic protection filter (not shown). The proximal portion 20 of spring coil 12 extends proximally in a U shape such that when unconstrained radially, the proximal portion 20 of spring coil 12 expands radially, causing the wire coil segment 16 to contract and frictionally engage the guidewire 14.

In certain embodiments, spring coil 12 may be formed as a separate component, and then attached to the intravascular device proximal end 22 prior to insertion in the patient. Attachment of the spring coil 12 to the intravascular device proximal end 22 may be accomplished by any number of suitable attachment means, including soldering, welding, crimping and/or adhesive bonding. In other embodiments, the spring coil 12 and intravascular device may be formed as a single member using, for example, a mold injection process.

Spring coil 12 may be formed of any number of suitable materials biocompatible with the body. For example, spring coil 12 may be formed of a metal such as 303 or 316 stainless steel. Alternatively, the spring coil 12 may be formed of a polymeric material such as polypropylene (PP), polyvinyl chloride (PVC), polyethylene and/or polytetrafluoroethylene (PTFE). In one particular implementation, spring coil 12 may comprise a shape-memory material such as nickel-titanium alloy (Nitinol).

A placement tube 26 can be used to advance the anchoring mechanism 10 to a desired location within a blood vessel, and to actuate the spring coil 12 between the locked and unlocked positions. Placement tube 26 has an inner lumen 28 configured to disengage spring coil 12 from the guidewire 14 when disposed about the proximal portion 20. As shown in FIG. 1, placement tube 26 can be used to compress the proximal portion 20 of spring coil 12 inwardly towards the guidewire 14, causing the wire coil segment 16 to expand slightly to permit the spring coil 12 to slide and rotate about the guidewire 14.

Figure 2:
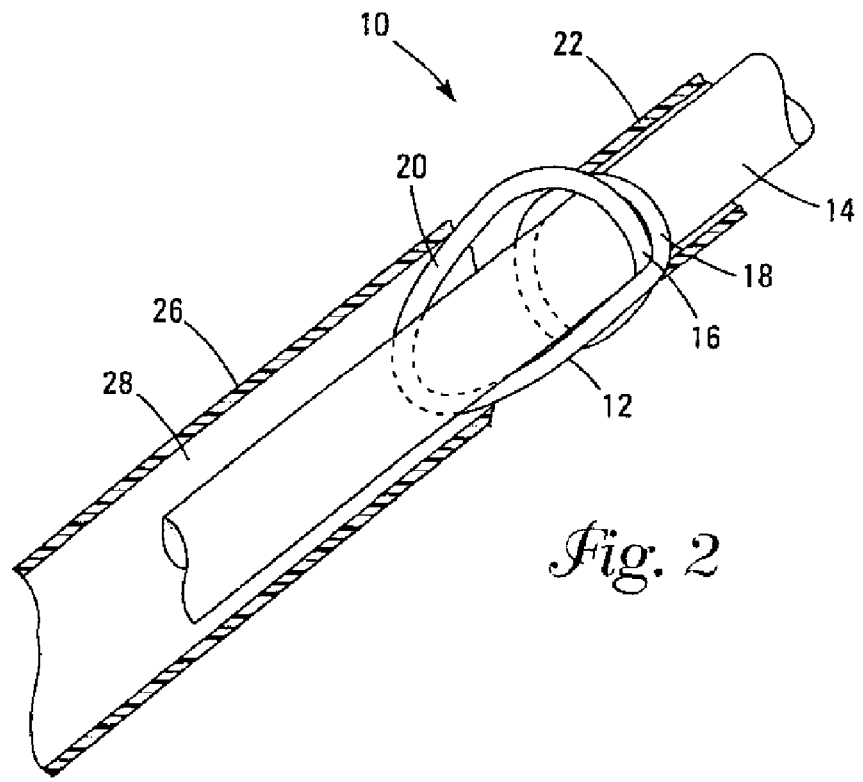
FIG. 2 is another cross-sectional view of the anchoring mechanism of FIG. 1, wherein the anchoring mechanism is releasable secured to the guidewire.

To engage the anchoring mechanism 10 along the guidewire 14, placement tube 26 is withdrawn proximally until the proximal portion 20 of spring coil 12 is unconstrained within the inner lumen 28, as shown in FIG. 2. Once unconstrained by the placement tube 26, the proximal portion 20 of spring coil 12 expands radially, causing the wire coil segment 16 to compress about the guidewire 14.

To release the anchoring mechanism 10 from the guidewire 14, placement tube 26 can be advanced distally along guidewire 14 until the proximal portion 20 is contained at least in part within inner lumen 28. Continued advancement of the placement tube 26 distally compresses the proximal portion 20, forcing the wire coil segment 16 to expand outwardly and disengage from the guidewire 14. Once disengaged from the guidewire 14, the anchoring mechanism 10 and attached intravascular device can then be withdrawn from the patient's body.

FIG. 3 illustrates an anchoring mechanism 110 in accordance with another exemplary embodiment of the present invention. Anchoring mechanism 110 comprises a split tube segment 112 having a proximal section 134, a distal section 136, and a bend region 138. The distal section 136 of split tube segment 112 is biased to deflect inwardly to frictionally engage the guidewire 14.

A placement tube 126 can be utilized to advance the split tube segment 112 along the guidewire 14, and to actuate the distal section 136 between the unlocked and locked positions. Placement tube 126 has a proximal portion (not shown) and a distal portion 130. The distal portion 130 of placement tube 126 includes a reduced outer diameter portion 132 having an outer diameter that is smaller than the inner diameter of split tube segment 112, allowing the split tube segment 112 to slide thereon, thereby preventing the distal section 136 of split tube segment 112 from frictionally engaging the guidewire 14.

To frictionally engage the anchoring mechanism 110 about the guidewire, placement tube 126 is retracted proximally along the guidewire 14, permitting the distal section 136 of the split tube segment 112 to deflect inwardly and compress against the guidewire 14, as shown in FIG. 4. To disengage the anchoring mechanism 110 from the guidewire 14, placement tube 126 can be advanced distally, forcing the distal section 136 of split tube segment 112 to disengage from the guidewire 14.

In the exemplary embodiment illustrated in FIGS. 3-4, split tube segment 112 is configured to function as a proximal stop for embolic protection filter 114, preventing movement of the filter 114 proximally thereof. As with any of the embodiments described herein, however, the split tube segment 112 may be attached to, or form part of, an embolic protection filter 114. In such cases, the anchoring mechanism may be utilized to releasably secure the embolic protection filter 114 directly to the guidewire 14.

In another exemplary embodiment illustrated in FIG. 5, an anchoring mechanism 210 in accordance with the present invention may include one or more leaf clamps. Anchoring mechanism 210 comprises a tube segment 212 having a proximal section 234, a distal section 236, and a bend region 238. The distal section 236 of tube segment 212 is biased to bend inwardly towards the guidewire 14, forming one or more leaf clamps adapted to frictionally engage the guidewire 14 in a locked position.

A placement tube 226 can be utilized to advance the tube segment 212 along the guidewire 14, and to actuate the distal section 236 between the unlocked and locked positions. Placement tube 226 has a distal section 230 having an outer diameter that is smaller than the inner diameter of the tube segment 212, allowing the distal section 230 of placement tube 226 to slide within tube segment 212. When placement tube 226 is inserted within tube segment 212 distal the bend region 238, the distal section 236 of tube segment 212 is substantially prevented from engaging the guidewire 14, as shown in FIG. 5.

To engage the anchoring mechanism 210 along the guidewire 14, placement tube 226 is retracted proximally until the distal section 230 of the placement tube 226 is proximal bend region 238, permitting the distal section 236 of the tube segment 212 to deflect inwardly and compress against the guidewire 14, as shown in FIG. 6. To subsequently release the lock, placement tube 226 can be advanced distally, forcing the distal section 236 of tube segment 112 to disengage from the guidewire 14.

Figure 7:
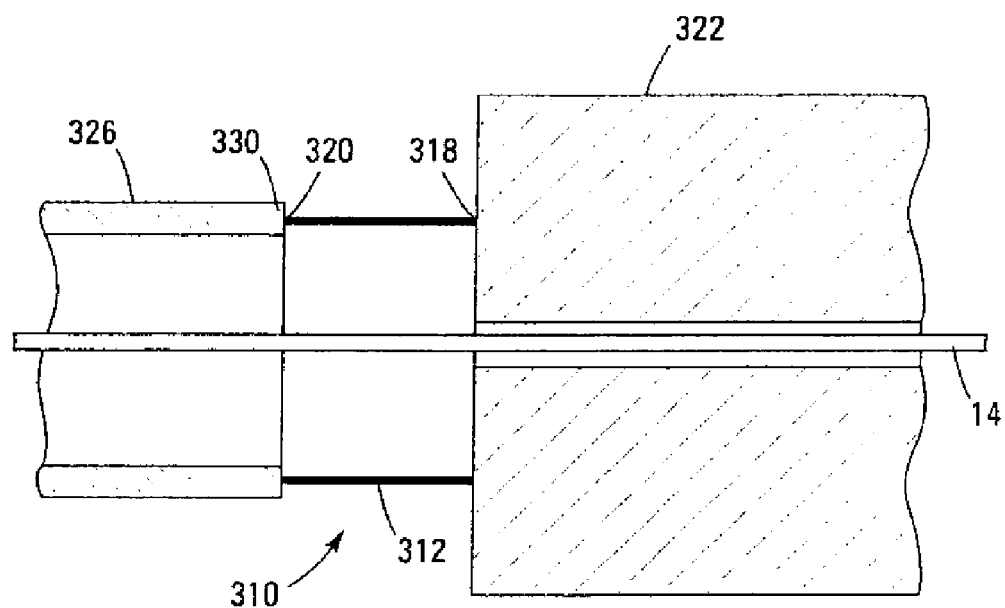
FIG. 7 is a cross-sectional view of an anchoring mechanism in accordance with another embodiment of the present invention, wherein the anchoring mechanism includes one or more wires.

FIG. 7 illustrates an anchoring mechanism 310 in accordance with another exemplary embodiment of the present invention. Anchoring mechanism 310 comprises a tubular member 326 and one or more wires 312 adapted to frictionally engage the guidewire 14 in a locked position. Tubular member 326 has a proximal end (not shown) and a distal end 330. Each wire 312 is attached at a distal end 318 to the proximal end 322 of an intravascular device (e.g. an embolic protection filter). The proximal end 320 each wire 312, in turn, is attached to the distal end 330 of the tubular member 326.

Figure 8:
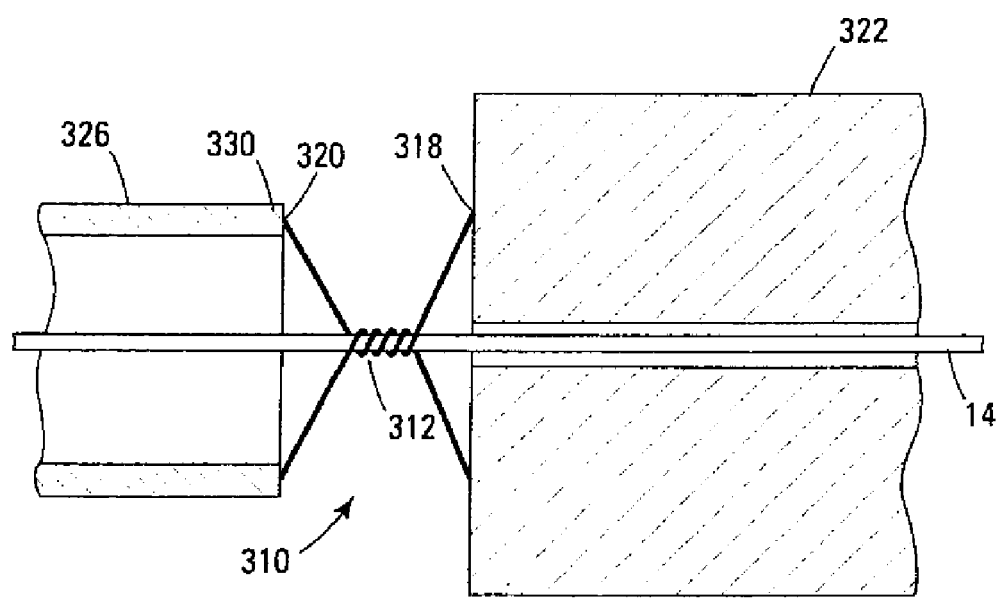
FIG. 8 is another cross-sectional view of the anchoring mechanism of FIG. 7, wherein the anchoring mechanism is releasably secured to the guidewire.

To engage the anchoring mechanism 310 along the guidewire 14, tubular member 326 is rotated in either a clockwise or counterclockwise direction until the one or more wires 312 frictionally engage the guidewire 14, as shown in FIG. 8. If desired, an optional coating can be applied to the wires 312 and/or the guidewire 14 to increase the frictional force therebetween.

To subsequently release the anchoring mechanism 310 from the guidewire 14, placement tube 326 can be rotated in an opposite direction until the one or more wires 312 disengage from the guidewire 14. Once disengaged, the anchoring mechanism 310 and intravascular device can then be removed from the patient's body.

In a similar embodiment illustrated in FIG. 95 an anchoring mechanism 410 in accordance with an exemplary embodiment of the present invention may include a tubular member 426 and a spring 412. Spring 412 is formed of a flexible wire having a distal end 418 and a proximal end 420. The distal end 418 of spring 412 is attached to the proximal portion 422 of an embolic protection filter. The proximal end 420 of spring 412, in turn, is attached the distal end 430 of tubular member 426.

Figure 9:
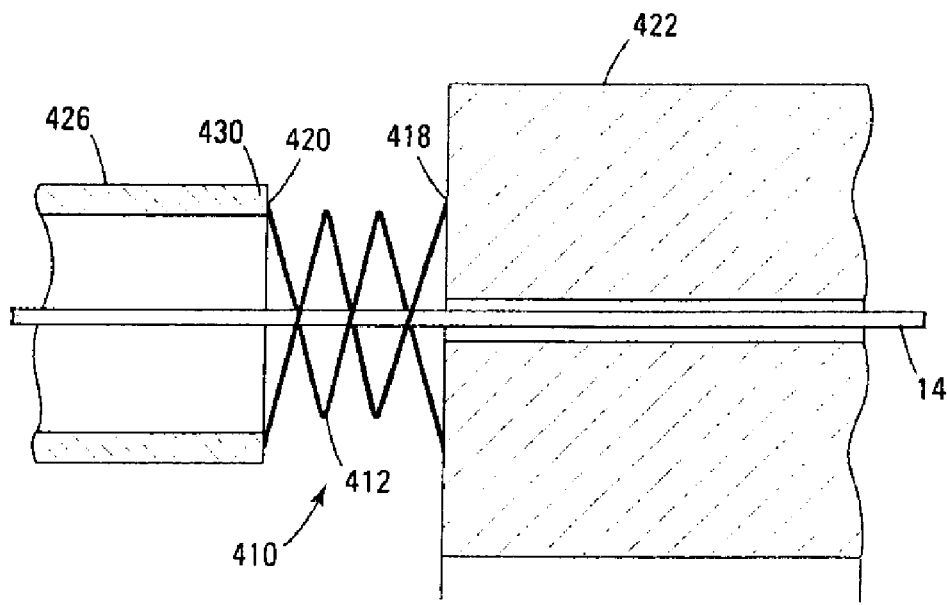
FIG. 9 is a cross-sectional view of an anchoring mechanism in accordance with another embodiment of the present invention, wherein the anchoring mechanism includes a spring.
Figure 10:
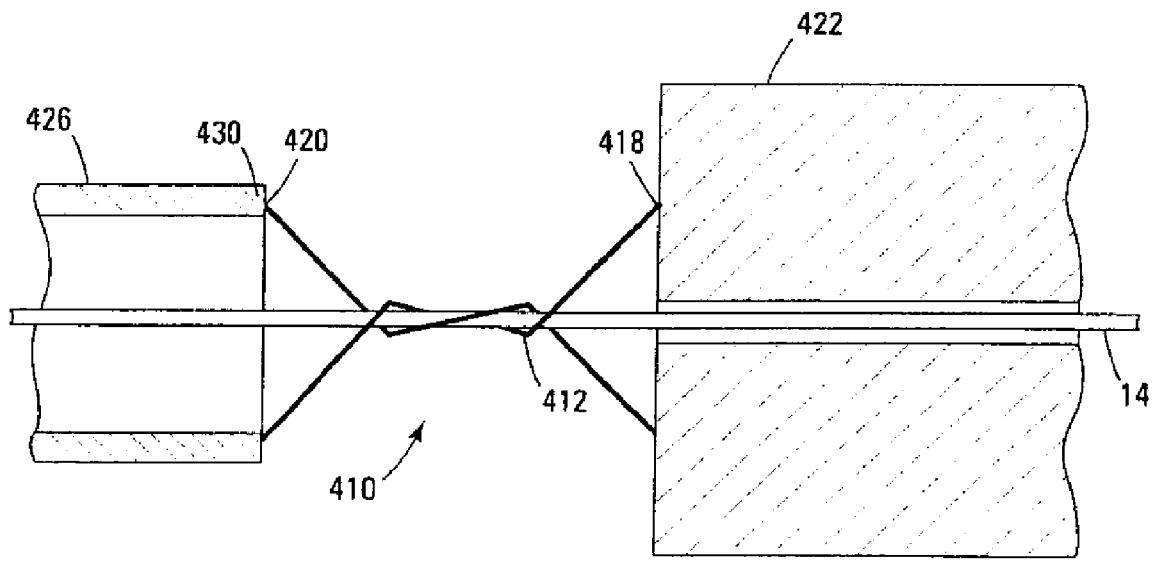
FIG. 10 is another cross-sectional view of the anchoring mechanism of FIG. 9, wherein the anchoring mechanism is releasably secured to the guidewire.

In an unlocked position illustrated in FIG. 9, spring 412 is adapted to slide and rotate about guidewire 14, allowing the intravascular device to be advanced along the guidewire 14 and placed at a desired location within the body. To engage the spring 412 along the guidewire 14, tubular member 426 is withdrawn proximally, forcing the spring 412 to stretch axially and compress radially about the guidewire 14. As with the previous embodiment, an optional coating can be applied to increase the frictional force between the guidewire 14 and the spring 412.

Figure 11:
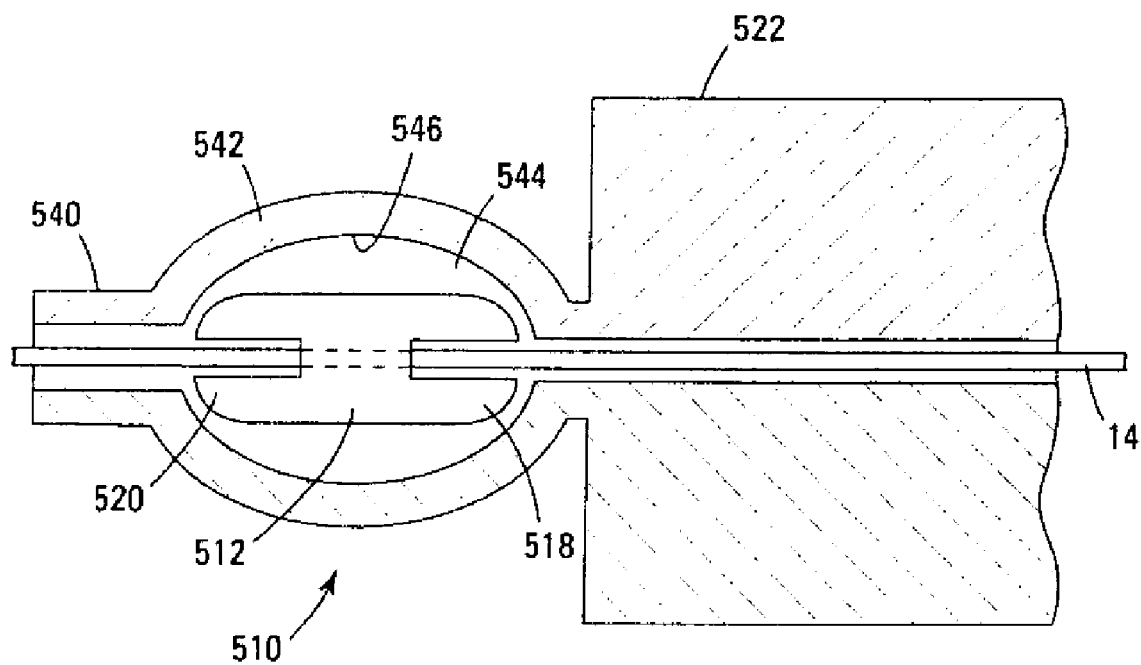
FIG. 11 is a cross-sectional view of an anchoring mechanism in accordance with another embodiment of the present invention, wherein the anchoring mechanism includes a cam.

In another exemplary embodiment illustrated in FIG. 11, an anchoring mechanism 510 in accordance with the present invention may employ a cam. Anchoring mechanism 510 comprises a tube segment 540 coupled to a proximal portion 522 of an embolic protection filter (not shown). Tube segment 540 includes an expanded portion 542 defining an inner chamber 544 having an inner wall surface 546.

Disposed within inner chamber 544 is an object 512 having a distal section 518 and a proximal section 520. The distal and/or proximal sections 518, 520 may each include a notch that permits the object ends 518, 520 to bend inwardly when compressed radially against the inner wall surface 546 of inner chamber 544.

In a first (i.e. unlocked) position illustrated in FIG. 11, the object 512 is positioned within chamber 544 such that neither the proximal end 520 nor the distal end 518 of object 512 is in contact with the inner wall surface 546. In this position, the object 512 is slidably and rotationally disposed along the guidewire 14, allowing the intravascular device to be placed within the patient's vasculature.

To engage the anchoring mechanism 510 along the guidewire 14, the tube segment 540 and attached intravascular device can be moved along the guidewire 14, forcing the object 512 disposed within the chamber 544 to compress against the inner wall surface 546. Continued advancement of the tube segment 540 along the guidewire 14 forces one of the notched ends (e.g. proximal end 520) to bend inwardly and frictionally engage the guidewire 14, as shown in FIG. 12.

Figure 12:
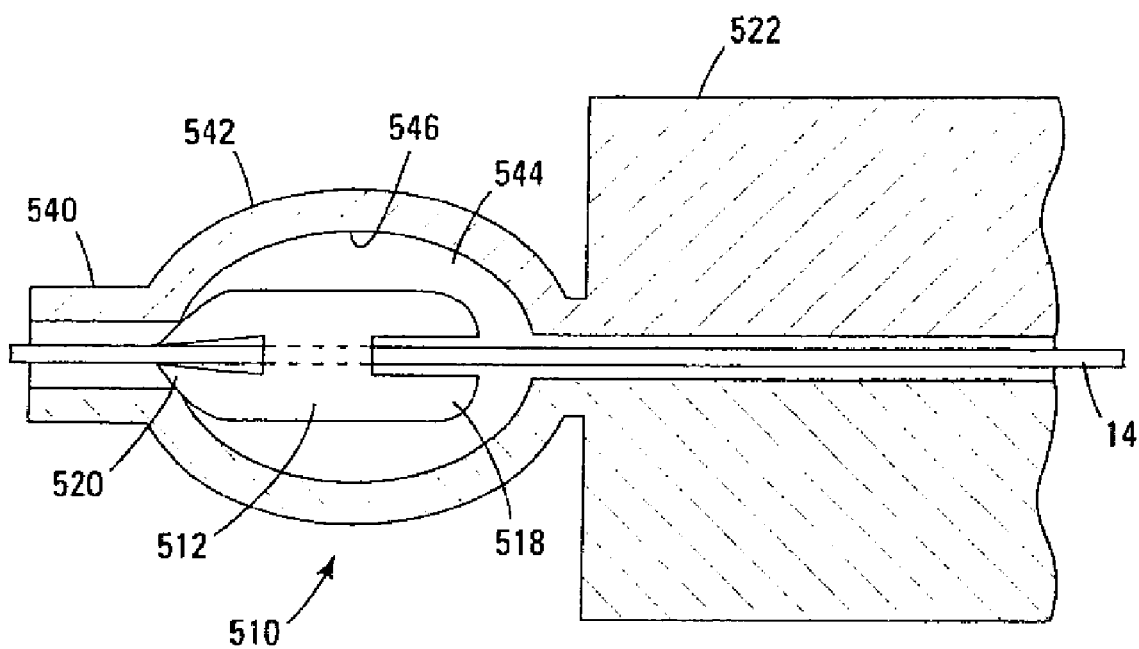
FIG. 12 is another cross-sectional view of the anchoring mechanism of FIG. 11, wherein the anchoring mechanism is releasably secured to the guidewire.

Although the exemplary embodiment illustrated in FIGS. 11-12 shows an object having a notch formed on or both ends, it is contemplated that other objects can be utilized without deviating from the scope of the invention. In certain embodiments, for example, the object may comprise a ball, wedge or coil. In other embodiments, the geometry of the inner wall surface may be circular, rectangular or have an irregular shaped surface.

Figure 13:
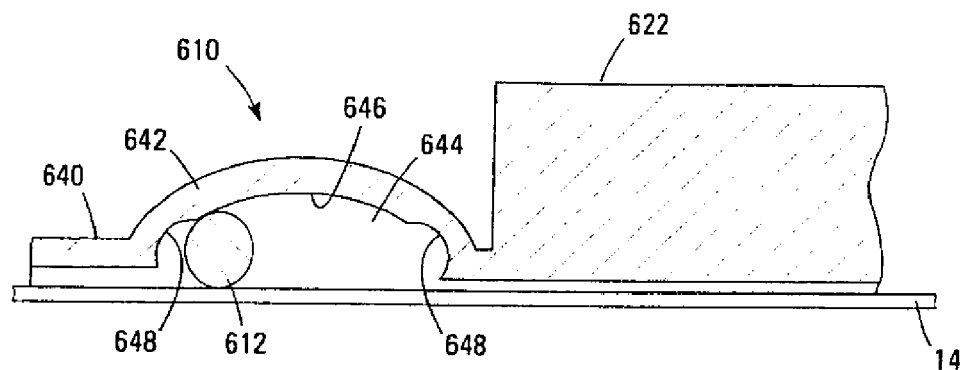
FIG. 13 is a cross-sectional view of an anchoring mechanism in accordance with another embodiment of the present invention employing a cam.
Figure 14:
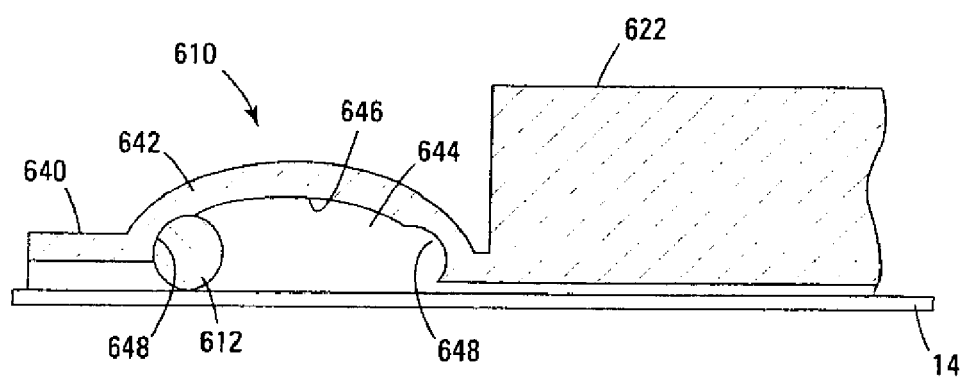
FIG. 14 is another cross-sectional view of the anchoring mechanism of FIG. 13, wherein the anchoring mechanism is releasably secured to the guidewire.
Figure 15:
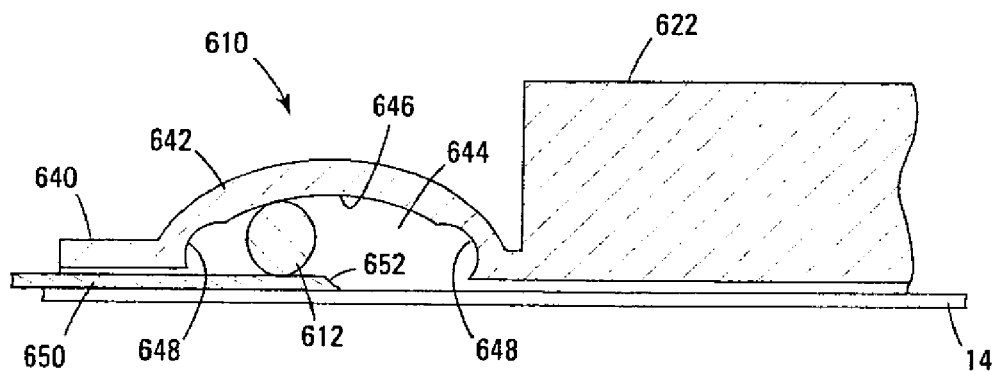
FIG. 15 is yet another cross-sectional view of the anchoring mechanism of FIG. 13, wherein a decoupling tube is utilized to disengage the anchoring mechanism from the guidewire.

In one such variation illustrated in FIGS. 13-15, an anchoring mechanism 610 in accordance with an exemplary embodiment of the present invention comprises a circular object 612 disposed within a chamber 644 having an irregularly shaped inner wall surface 646. The inner wall surface 646 of tube segment 642 includes one or more recesses 648 substantially conforming in size and shape to the dimensions of the circular object 612.

In an first (i.e. unlocked), the circular object 612 is positioned within the inner chamber 644 such that the object 612 is not in contact with either of the recesses 648. To engage the anchoring mechanism 610 along the guidewire 14, tube segment 640 is moved along the guidewire 14 until the circular object 612 locks into one of the recesses 648, as shown in FIG. 14.

To disengage the anchoring mechanism 610 from the guidewire 14, a decoupling 15 tube 650 can be advanced along the guidewire 14 to disengage the circular object 612 from the recessed surface 648, as shown in FIG. 15. The distal end 652 of the decoupling tube 650 may have a geometry corresponding in size and shape to the particular object employed. For example, the distal end 652 of decoupling tube 650 may be curved slightly to correspond with the shape of the circular object 612.

Figure 16:
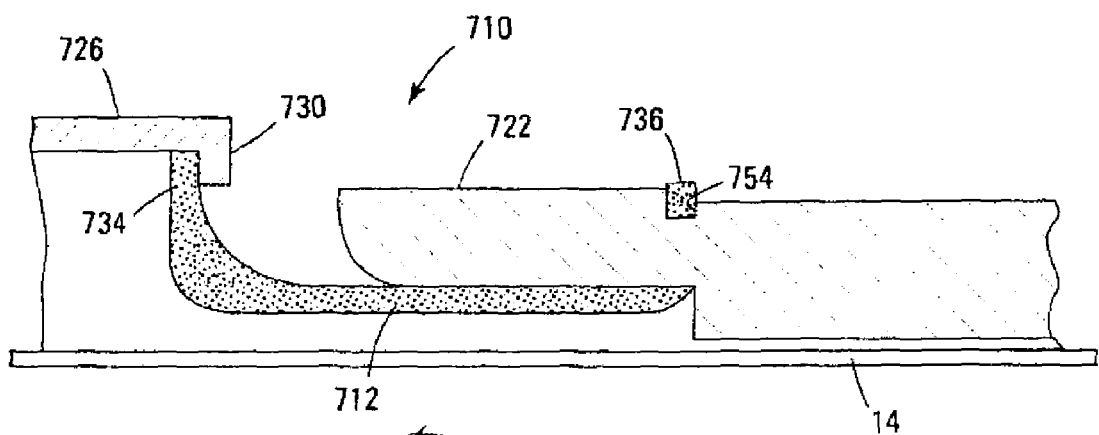
FIG. 16 is a cross-sectional view of an anchoring mechanism in accordance with another embodiment of the present invention, wherein the anchoring mechanism includes an elastomeric object.

FIG. 16 illustrates an anchoring mechanism 710 in accordance with another exemplary embodiment of the present invention. An elastomeric object 712 is coupled to a reduced inner diameter portion 722 disposed on the proximal end 722 of an embolic protection filter (not shown). The elastomeric object 712 is attached at a distal end 736 to the reduced inner diameter portion 722 at notch 754, and at a proximal end 734 to a placement tube 726. In use, the elastomeric object 712 is configured to lock onto the guidewire 14 when unconstrained by a tab disposed on the distal end 730 of the placement tube 726.

Figure 17:
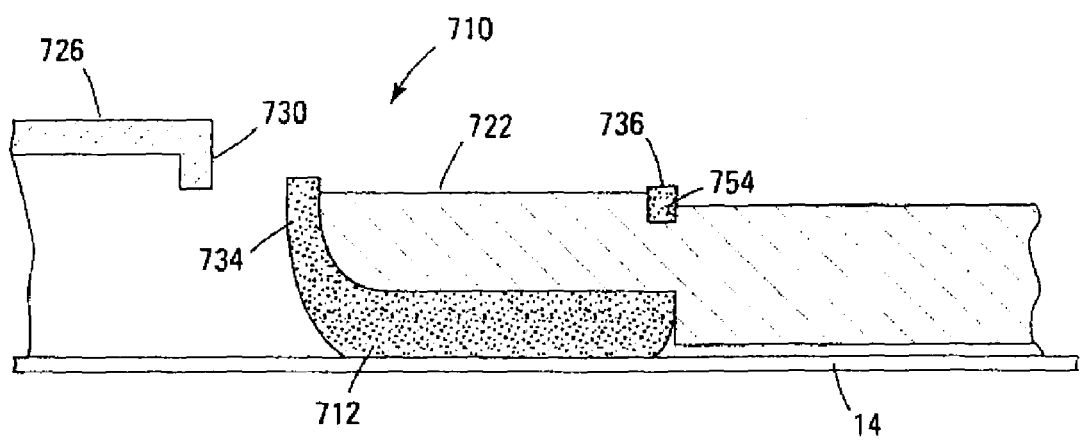
FIG. 17 is another cross-sectional view of the anchoring mechanism of FIG. 16, wherein the anchoring mechanism releasably secured to the guidewire.

In a first (i.e. unlocked) position illustrated in FIG. 16, placement tube 726 is configured to attach to a proximal end 734 of the elastomeric object 712, causing it to stretch axially and disengage from the guidewire 14. To engage the anchoring mechanism 710 along the guidewire 14, placement tube 726 is retracted proximally, causing the proximal end 734 of the elastomeric object 712 to detach from the tab on the distal end 730 of the placement tube 726. Once detached, the elastomeric object 712 reverts to its natural, pre-stretched state, causing it to frictionally engage the guidewire 14, as shown in FIG. 17.

FIG. 18 illustrates an anchoring mechanism 810 in accordance with yet another exemplary embodiment of the present invention. Anchoring mechanism 810 comprises a shape memory tube 812 having a pre-defined shape which, when compressed radially by a placement tube 826, functions in an unlocked position, and when unconstrained radially, functions in a locked position. To bias the shape memory tube 812 to radially expand and frictionally engage the guidewire 14 in the locked position, a super elastic material such as a nickel titanium alloy (Nitinol) may be used.

In the exemplary embodiment illustrated in FIG. 18, the distal end 818 of shape memory tube 812 further includes a joint 856 adapted to permit rotation of the shape memory tube 812 relative to the proximal end 822 of embolic protection filter 814. In use, joint 856 permits rotation of the embolic protection filter within the patient's body while substantially preventing movement of the intravascular device along the guidewire 14.

A placement tube 826 may be utilized to advance the shape memory tube 812 and embolic protection filter 814 along the guidewire 14, and to actuate the shape memory tube 812 between the unlocked and locked positions. Placement tube 826 has a proximal end (not shown), a distal end 830, and an inner lumen 828. The inner lumen 828 is configured in size and shape to radially compress the shape memory tube 812 therein, allowing the anchoring mechanism 810 to slide and rotate about the guidewire 14. To engage the anchoring mechanism 810 along the guidewire 14, placement tube 826 can be withdrawn proximally, allowing the shape memory tube 812 to revert to its pre-defined shape and frictionally engage the guidewire 14, as shown in FIG. 19.

To disengage the anchoring mechanism 810 from the guidewire 14, placement tube 826 is advanced distally until the distal end 830 is located proximate and proximal the proximal end 820 of shape memory tube 812. Continued advancement of the placement tube 826 distally causes the shape-memory tube 812 to radially compress within inner lumen 828 and disengage from the guidewire 14. The distal end 830 of shape memory tube 812 may be flared slightly to facilitate advancement of the placement tube 826 about the shape memory tube 812.

Figure 20:
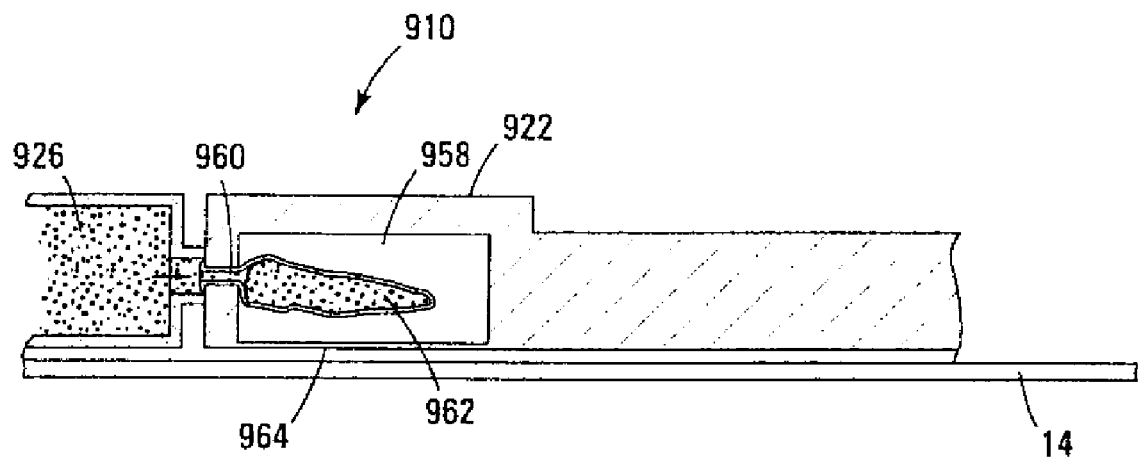
FIG. 20 is a cross-sectional view of an anchoring mechanism in accordance with another embodiment of the present invention, wherein the anchoring mechanism includes an expandable balloon.

FIG. 20 illustrates an anchoring mechanism 910 in accordance with yet another exemplary embodiment of the present invention. Anchoring mechanism 910 comprises a proximal end portion 922 of an embolic protection filter (not shown) containing an expandable lumen 958 having an inlet port 960 and an expandable balloon 962. A pressure source 926 in fluid communication with the inlet port 960 is adapted to provide fluidic pressure to the expandable balloon 962 to actuate the device between the unlocked and locked positions.

Figure 21:
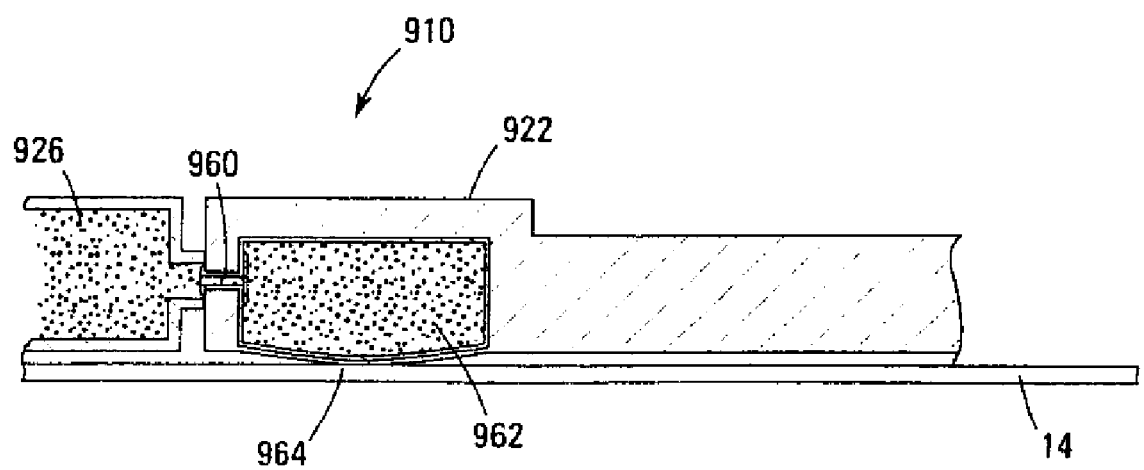
FIG. 21 is another cross-sectional view of the anchoring mechanism of FIG. 20, wherein the anchoring mechanism is releasably secured to the guidewire.

As shown in FIG. 21, when fluidic pressure from pressure source 926 is applied to inlet port 960, balloon 962 expands within expandable lumen 958 forcing the innermost portion 964 of the expandable lumen 958 to deflect inwardly and engage the guidewire 14. To disengage the anchoring mechanism 910 from the guidewire 14, fluid is evacuated from the balloon 962, causing the innermost portion 962 of the expandable lumen 958 to disengage from the guidewire 14.

Figure 22:
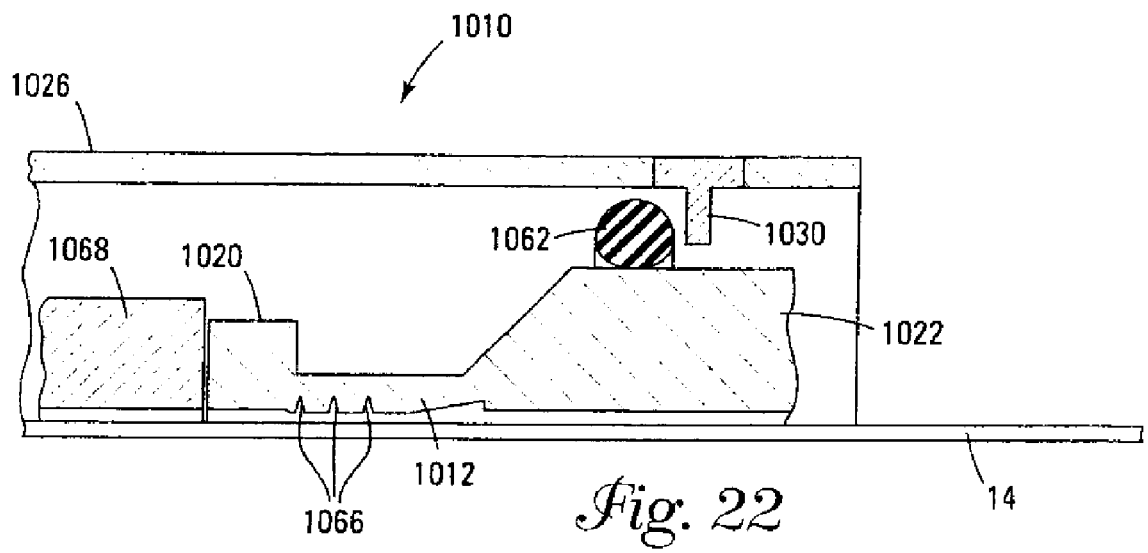
FIG. 22 is a cross-sectional view of an anchoring mechanism in accordance with another embodiment of the present invention, wherein the anchoring mechanism includes an O-ring.

FIG. 22 illustrates an anchoring mechanism 1010 in accordance with yet another exemplary embodiment of the present invention. Anchoring mechanism 1010 comprises a proximal portion 1022 of an embolic protection filter (not shown) having a deflectable section 1012 thereon actuatable between an unlocked (i.e. disengaged) position and a locked (i.e. engaged) position.

Deflectable section 1012 has a relatively small outer diameter, allowing the deflectable section 1012 to deflect radially and compress along the guidewire 14 when an elastomeric O-ring 1062 is disposed thereon. One or more notches 1066 disposed at various locations along the inner diameter of deflectable section 1012 may also be employed to engage the deflectable section 1012 along the guidewire 14.

Figure 23:
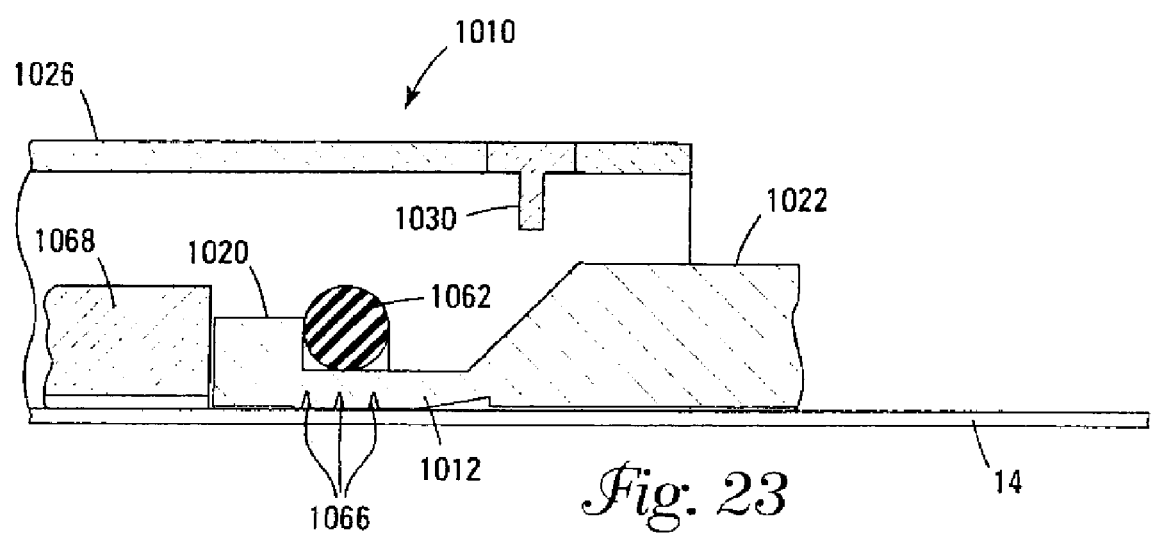
FIG. 23 is another cross-sectional view of the anchoring mechanism of FIG. 22, wherein the anchoring mechanism is releasably secured to the guidewire.

In a first position shown in FIG. 22, deflectable section 1012 is disengaged from the guidewire 14, allowing the intravascular device to slide and rotate about the guidewire 14. To engage the anchoring mechanism 1010 along the guidewire 14, a push tube 1068 is positioned proximate and proximal the proximal end 1020 of the intravascular device. Holding the intravascular device stationary with push tube 1068, a placement tube 1026 having an inwardly facing tab 1030 is withdrawn proximally, forcing the O-ring 1062 to slide proximally to a second position about the deflectable section 1012, as shown in FIG. 23. The inward force exerted by the O-ring 1062 forces the deflectable section 1012 to bend inwardly and compress against the guidewire 14.

Figure 24:
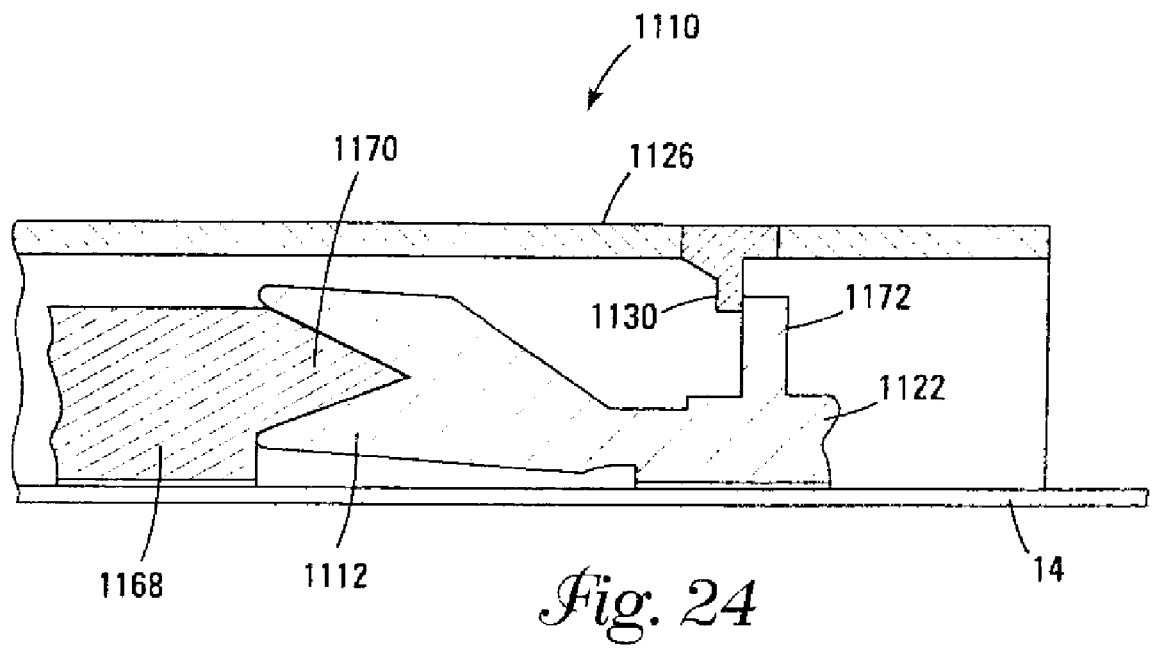
FIG. 24 is a cross-sectional view of an anchoring mechanism in accordance with another embodiment of the present invention, wherein the anchoring mechanism includes one or more deflectable tabs.

FIG. 24 illustrates an anchoring mechanism 1110 in accordance with yet another exemplary embodiment of the present invention. Anchoring mechanism 1110 comprises a placement tube 1126, a push tube 1168 and a plurality of radial tabs 1112 extending from the proximal portion 1122 of an embolic protection filter (not shown). The deflectable radial tabs 1112 are biased inwardly such that when unconstrained by push tube 1168, the radial tabs 1112 deflect inwardly towards the guidewire 14.

Push tube 1168 includes a tapered distal end 1170 having a size and shape that corresponds with the size and shape of the deflectable radial tabs 1112. The placement tube 1126 includes one or more inwardly facing tabs 1130 that can be utilizing to transport the anchoring mechanism 1110 along the guidewire 14, and to subsequently release the anchoring mechanism 1110 once engaged.

Figure 25:
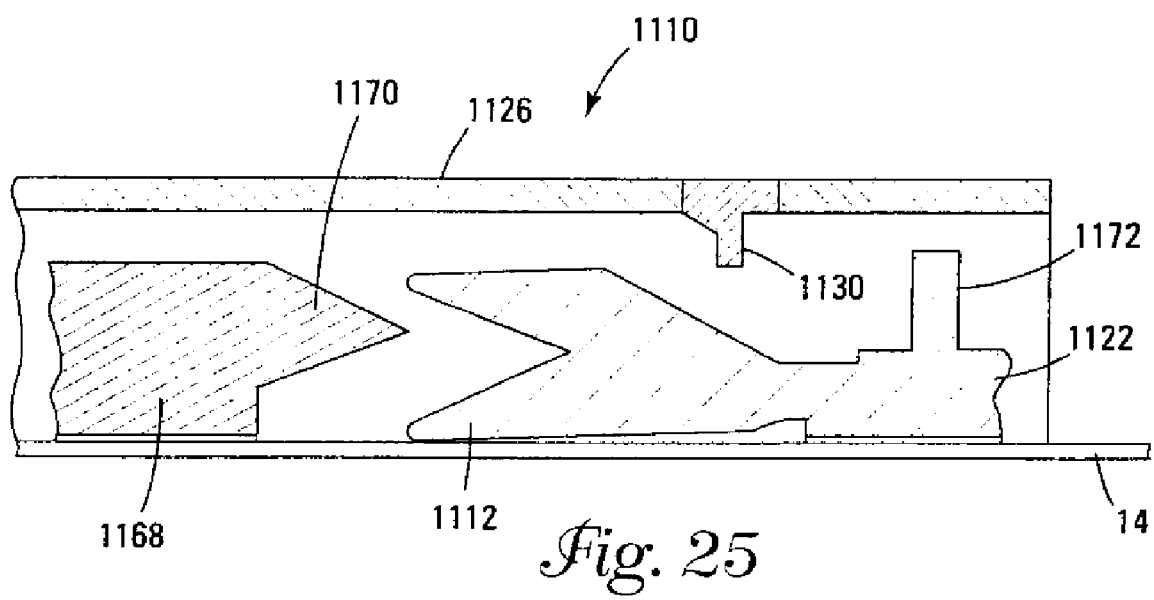
FIG. 25 is another cross-sectional view of the anchoring mechanism of FIG. 24, wherein the anchoring mechanism is releasably secured to the guidewire.

To engage the anchoring mechanism 1110 along the guidewire 14, push tube 1168 is retracted proximally until the deflectable radial tabs 1112 are unconstrained by the tapered distal end 1170 of push tube 1168. Once unconstrained, the radial tabs 1112 deflect inwardly and frictionally engage the guidewire 14, as shown in FIG. 25. Once engaged, the placement tube 1126 can then be retracted proximally, causing the embolic protection filter to deploy within the patient's vessel.

To disengage the anchoring mechanism 1110 from the guidewire 14, placement tube 1126 is advanced distally until the one or more tabs 1130 are positioned proximate and proximal a corresponding tab 1172 located on the embolic protection filter. Continued advancement of the placement tube 1126 distally causes the one or more inwardly facing tabs 1130 to bend slightly, allowing the one or more radial tabs 1130 to displace distal the corresponding tab 1172 located on the embolic protection filter. The push tube 1168 can then be advanced distally, forcing the deflectable radial tabs 1112 to disengage the anchoring mechanism 1110 from the guidewire 14.

Figure 26:
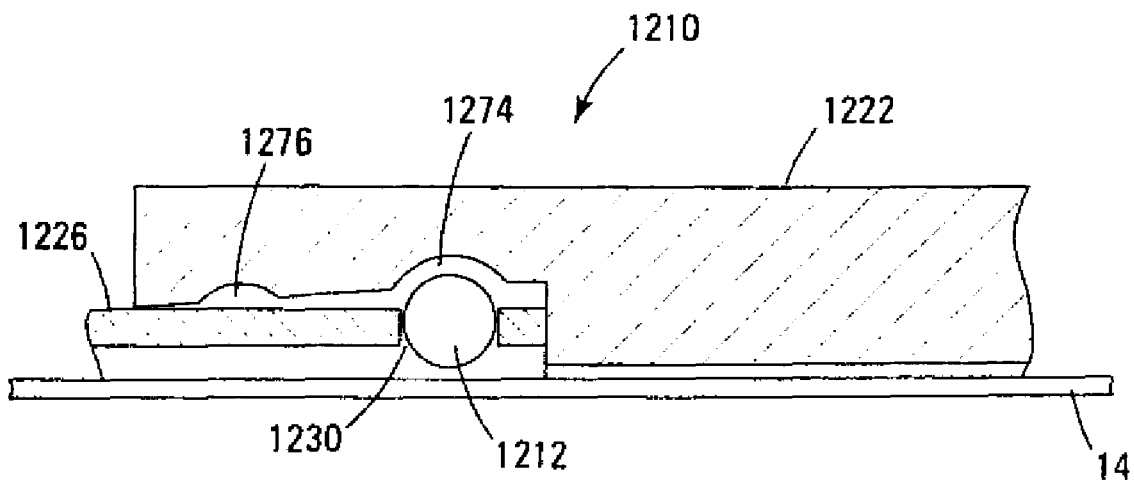
FIG. 26 is a cross-sectional view of an anchoring mechanism in accordance with another embodiment of the present invention, wherein the anchoring mechanism includes a circular object.
Figure 27:
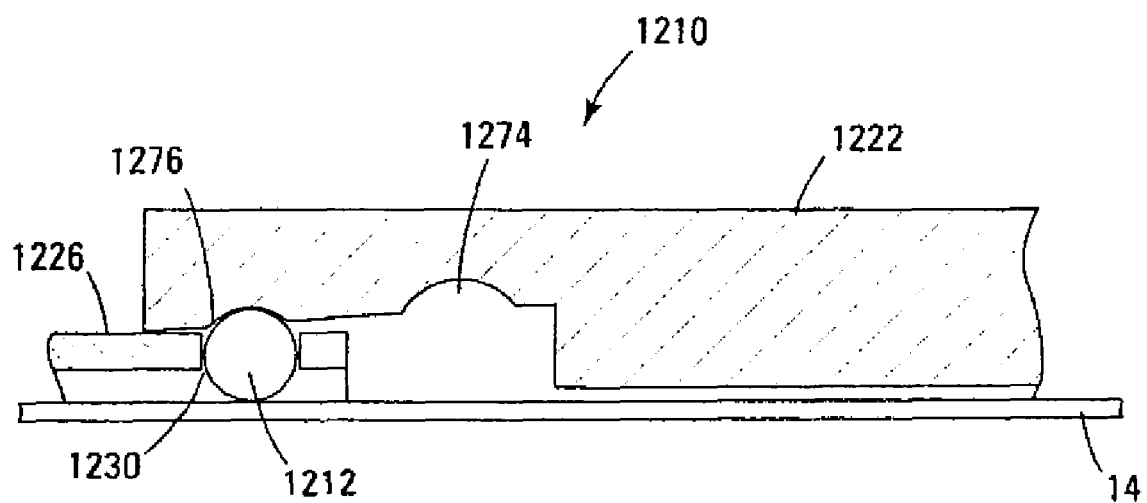
FIG. 27 is another cross-sectional view of the anchoring mechanism of FIG. 26, wherein the anchoring mechanism is releasably secured to the guidewire.

FIG. 26 illustrates an anchoring mechanism 1210 in accordance with yet another exemplary embodiment of the present invention. Anchoring mechanism 1210 comprises a circular object 1212, a placement tube 1226 having an opening 1230 adapted to contain the circular object 1212, and two recesses 1274, 1276 disposed on the proximal portion 1222 of an embolic protection filter (not shown). The anchoring mechanism 1210 is slidably and rotationally disposed along the guidewire 14 when the circular object 1212 is engaged within the first (i.e. larger) recess 1274, and releasably secured to the guidewire 14 when the circular object 1212 is engaged within the second (i.e. smaller) recess 1276.

In a first position illustrated in FIG. 26, the circular object 1212 is disposed within the first recess 1274. The first recess 1274 is configured in size and shape to allow the circular object 1212 to rotate therein, allowing the anchoring mechanism 1210 to be moved along the guidewire 14. To engage the anchoring mechanism 1210 along the guidewire 14, placement tube 1226 is withdrawn proximally until the circular object 1212 engages the second recess 1276, as shown in FIG.

27. The second recess 1276 has a smaller inner diameter such that, when the circular object 1212 is retracted from the first recess 1274 to the second recess 1276, the circular object 1212 compresses against the guidewire 14.

Figure 28:
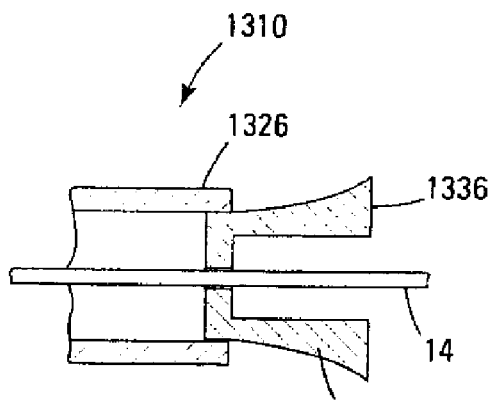
FIG. 28 is a cross-sectional view of an anchoring mechanism in accordance with another embodiment of the present invention, wherein the anchoring mechanism includes a flared collet.

FIG. 28 illustrates an anchoring mechanism 1310 in accordance with yet another exemplary embodiment of the present invention employing a flared collet 1312. As shown in FIG. 28, the flared collet 1312 includes a reduced inner diameter distal portion 1336 that permits the collet 1312 to deflect inwardly and frictionally engage the guidewire 14 when compressed radially by a placement tube 1326.

Figure 29:
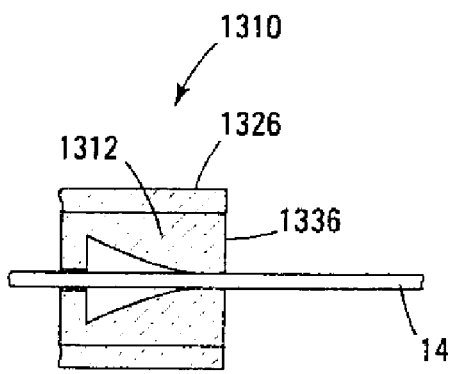
FIG. 29 is another cross-sectional view of the anchoring mechanism of FIG. 28, wherein the anchoring mechanism is releasably secured to the guidewire.

To engage the collet 1312 along the guidewire 14, placement tube 1326 is advanced distally, forcing the distal portion 1336 of the collet 1312 to bend inwardly and of frictionally engage the guidewire 14, as shown in FIG. 29. To disengage the collet 1312 from the guidewire 14, the placement tube 1326 is retracted proximally until the distal portion 1336 disengages from the guidewire 14.

Figure 30:
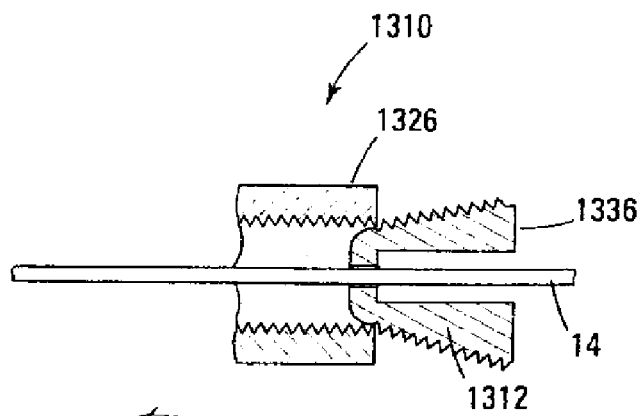
FIG. 30 is another cross-sectional view of the anchoring mechanism of FIG. 28, wherein the anchoring mechanism further includes threads.

In an alternative embodiment illustrated in FIG. 30, the inner diameter of placement tube 1326 may include threads adapted to engage a corresponding set of threads disposed on the outer diameter of the collet 1312. To engage the collet 1312 along the guidewire 14, placement tube 1326 is rotated until the threads on the placement tube 1326 engage the threads on the collet 1312. Continued rotation of the placement tube 1326 relative to the collet 1312 causes the collet 1312 to frictionally engage the guidewire 14 in a manner similar to that described with respect to FIG. 29.

Figure 31:
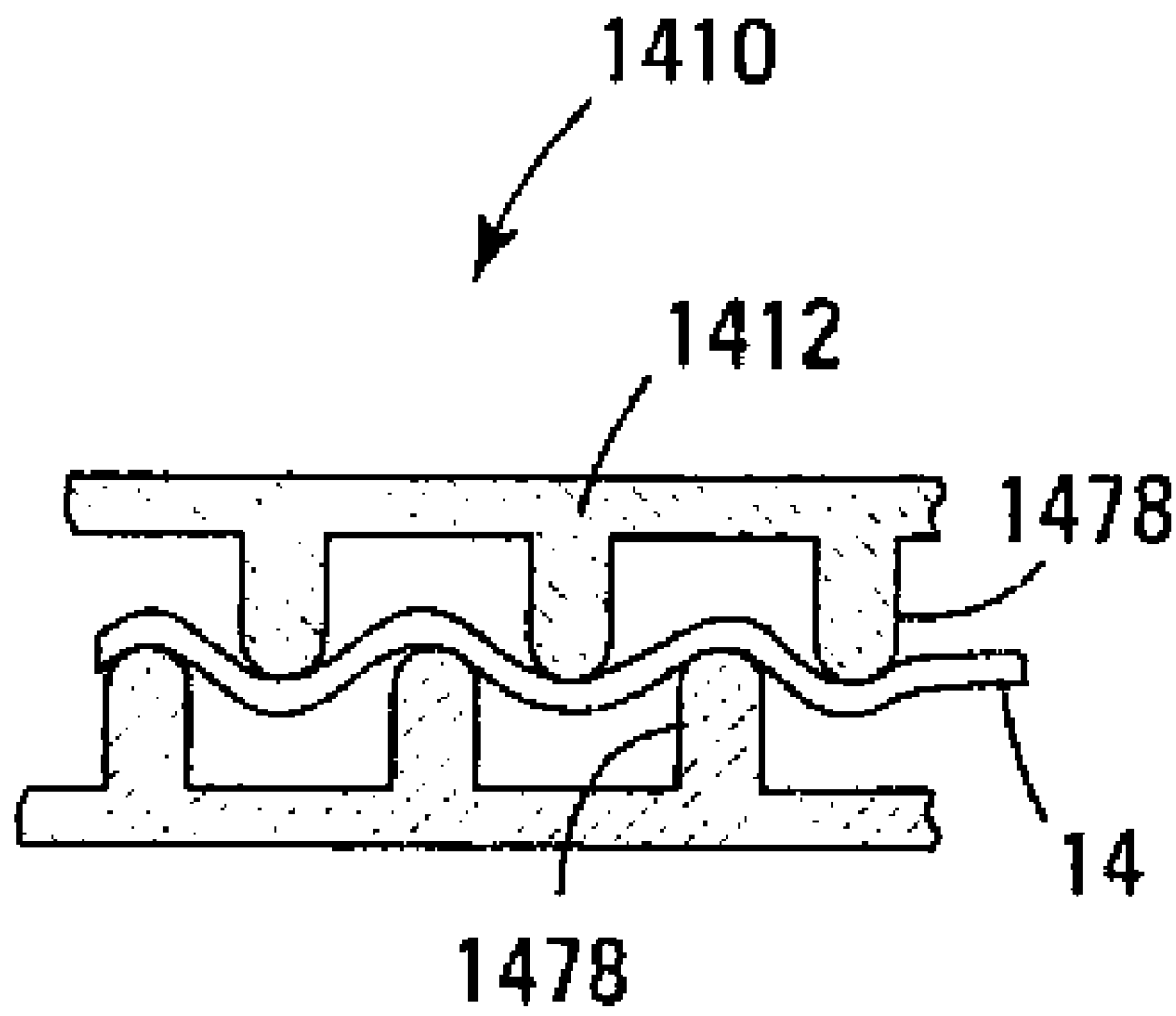
FIG. 31 is a cross-sectional view of an anchoring mechanism in accordance with another embodiment of the present invention, wherein the anchoring mechanism includes an off-set block.

FIG. 31 illustrates an anchoring mechanism 1410 in accordance with another exemplary embodiment of the present invention utilizing an offset block. Clamping mechanism 1410 comprises a tubular member 1412 having a plurality of radially offset tabs 1478 extending inwardly towards the guidewire 14. The offset tabs 1478 are staggered at various locations along the inner diameter of the tubular member 1412. In use, the radially offset tabs 1478 prevent movement of the anchoring mechanism 1410 along the guidewire 14 in the absence of a force applied thereto by the operator.

Figure 32:
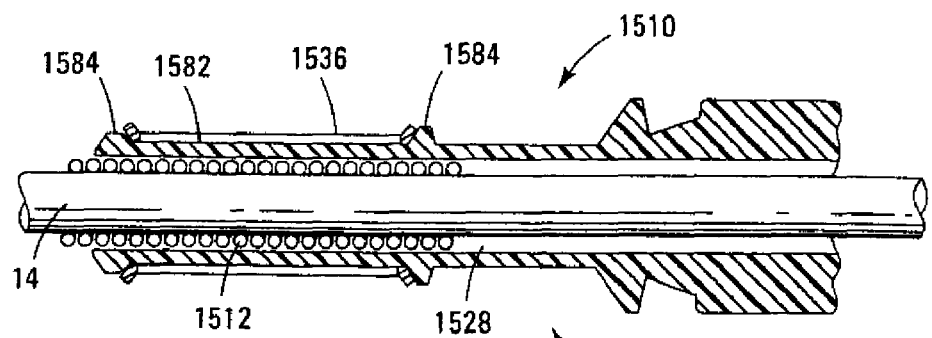
FIG. 32 is a cross-sectional view of an anchoring mechanism in accordance with another embodiment of the present invention, wherein the anchoring mechanism includes a split-jawed collet and a spring.

FIG. 32 illustrates yet another exemplary embodiment of the present invention utilizing a split jawed collet operatively coupled to a spring seat. As shown in a locked position in FIG. 32, anchoring mechanism 1510 comprises a proximal portion 1522 of an embolic protection filter having an inner lumen 1528 configured to receive the guidewire 14.

Secured within the inner lumen 1528 of proximal portion 1522 is a spring 1512 that is frictionally engageable along guidewire 14 in a locked position, and slidably and rotationally disposed about guidewire 14 in an unlocked position. Spring 1512 may be formed from a laser cut tube comprised of a shape memory material such as Nitinol. Alternatively, spring 1512 may be formed from a metal such as 303 or 316 stainless steel. In some embodiments, spring 1512 may be formed from a highly radiopaque material (e.g. 316L stainless steel or platinum) to permit fluoroscopic monitoring of the device.

Figure 33:
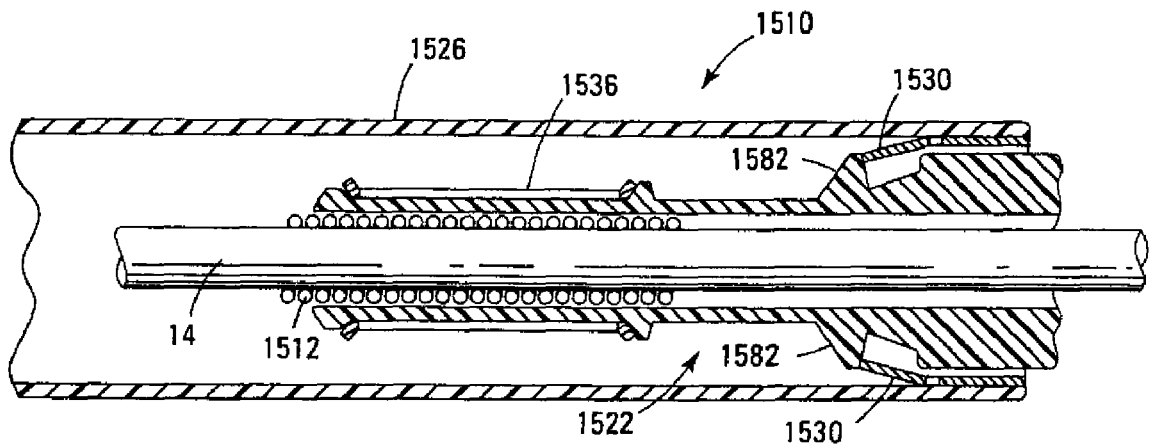
FIG. 33 is another cross-sectional view of the anchoring mechanism of FIG. 32, wherein a retrieval sheath is secured to the anchoring mechanism.

A split jawed collet 1536 disposed about a spring seat 1582 formed on the proximal portion 1522 of the embolic protection filter may be used to actuate the spring 1512 between the locked and unlocked positions. Split jawed collet 1536 can be formed from a split tubular member, similar to that shown with respect to FIGS. 28-29. In a locked position illustrated in FIG. 32, the split jawed collet 1536 compresses between several notches 1584 formed on seat 1582, which biases the spring 1512 axially, forcing the spring 1512 to frictionally engage the guidewire 14. To disengage the spring 1512 from the guidewire 14, the operator advances a retrieval sheath 1526 having one or more retrieval fingers 1530 distally until the one or more retrieval fingers 1530 lock onto a first enlarged outer diameter section 1582 formed on proximal portion 1522, as shown in FIG. 33. The one or more retrieval fingers 1530 are configured to bend in only a single direction, allowing the retrieval sheath 1526 to lock onto the proximal portion 1522 of the embolic protection filter. The one or more retrieval fingers 1530 may be formed from any number of suitable materials such as Nitinol, nylon, polyether-ether ketone (PEEK), etc.

Figure 34:
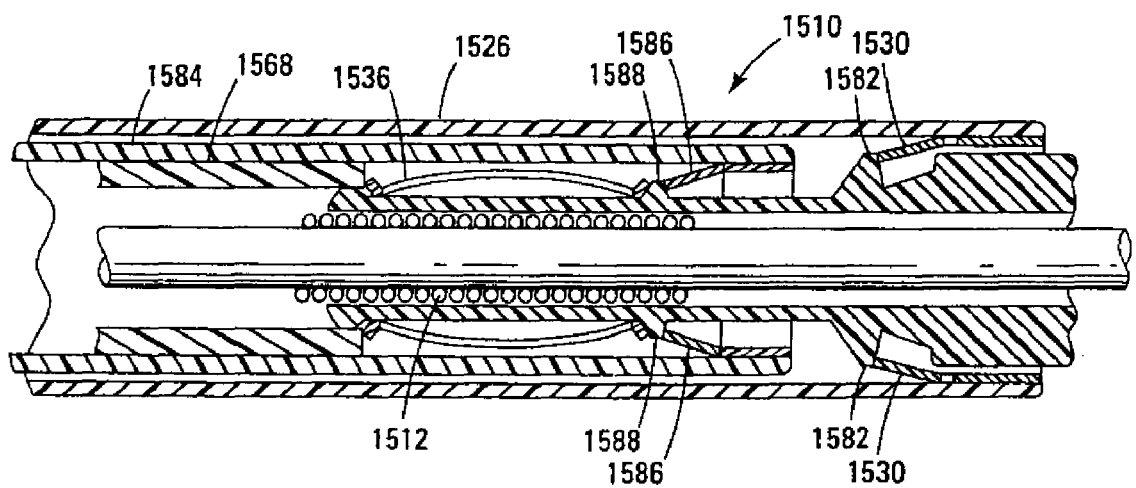
FIG. 34 is another cross-sectional view of the anchoring mechanism of FIG. 32, wherein a second sheath and decoupling tube are utilized to disengage the anchoring mechanism from the guidewire.

Once the retrieval sheath 1526 is engaged along the proximal portion 1522 of the filter, the operator next advances a second sheath 1584 along the guidewire until a second set of retrieval fingers 1586 engage a second enlarged outer diameter section 1588 formed on proximal portion 1522. Once the second set of retrieval fingers 1586 engage the second enlarged outer diameter section 1588, a push tube 1568 is advanced distally, forcing the split jaw collet 1536 to compress axially, causing the spring 1512 to frictionally disengage from the guidewire, as shown in FIG. 34. The embolic protection filter can then be retracted along guidewire 14 and removed from the patient's body, if desired.

Figure 35:
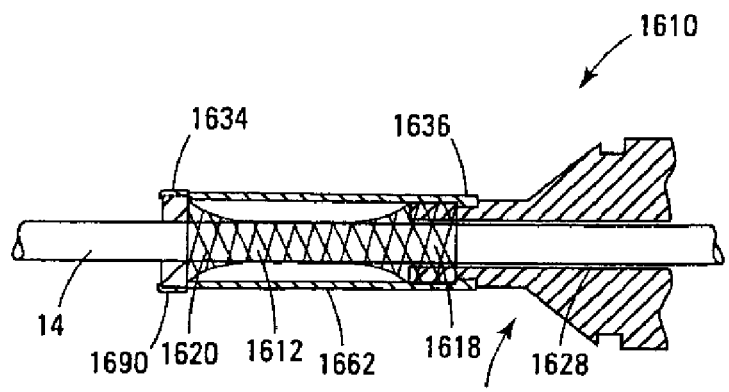
FIG. 35 is a cross-sectional view of an anchoring mechanism in accordance with another embodiment of the present invention, wherein the anchoring mechanism includes a sleeve.

FIG. 35 illustrates an anchoring mechanism 1610 in accordance with yet another exemplary embodiment of the present invention utilizing a sleeve 1612. Anchoring mechanism 1610 comprises a proximal portion 1622 of an embolic protection filter (not shown) having an inner lumen 1628 configured to receive the guidewire 14.

A spring 1662 attached to the proximal portion 1622 can be utilized to frictionally engage the sleeve 1612 along the guidewire 14. Spring 1662 has a proximal end 1634 and a distal end 1636. The proximal end 1634 of spring 1662 is attached to a tubular member 1690 slidably disposed along guidewire 14. The distal end 1636 of spring 1662 is fixedly attached to the proximal portion 1622 of the embolic protection filter.

Sleeve 1612 may be formed from a loosely braided material such as Dacron, and is configured to radially collapse when placed under tension by the spring 1662. The sleeve 1612 is secured at a distal end 1618 to the proximal portion 1622 of the filter. The proximal end 1620 of the sleeve, in turn, is attached to the tubular member 1690. In a locked position illustrated in FIG. 35, the spring 1662 forces the sleeve 1612 into tension axially, forcing the sleeve 1612 to radially compress and frictionally engage the guidewire 14.

Figure 36:
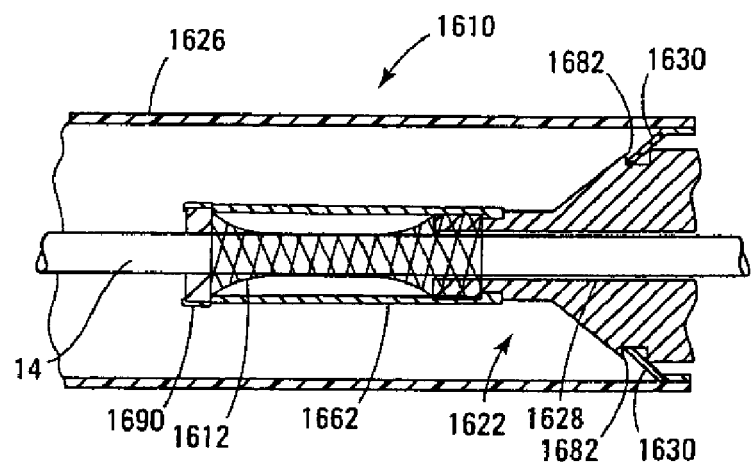
FIG. 36 is another cross-sectional view of the anchoring mechanism of FIG. 35, wherein a retrieval sheath is secured to the anchoring mechanism.
Figure 37:
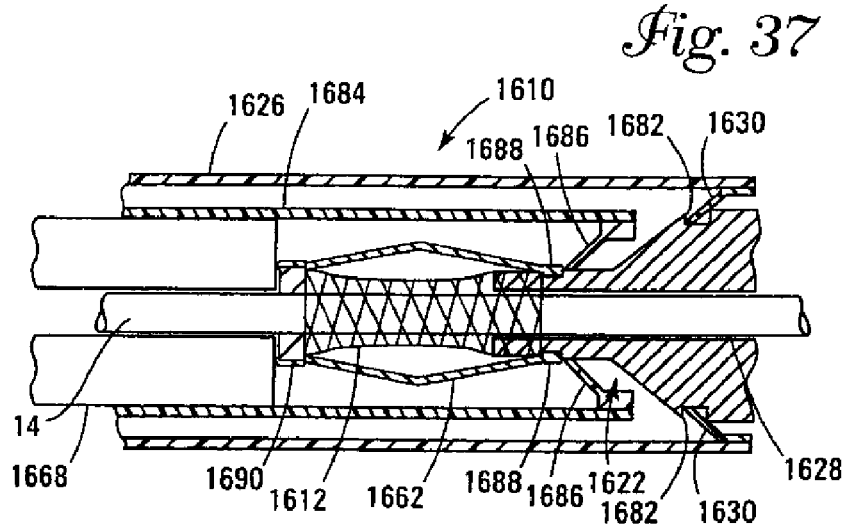
FIG. 37 is another cross-sectional view of the anchoring mechanism of FIG. 35, wherein a second sheath and decoupling tube are utilizing to disengage the anchoring mechanism from the guidewire.

To disengage the sleeve 1612 from the guidewire 14, the operator advances a retrieval sheath 1626 having one or more retrieval fingers 1630 distally along the guidewire 14 until the one or more retrieval fingers 1630 lock onto a first notch 1682 located on the proximal portion 1622, as shown in FIG. 36. Once the retrieval sheath 1626 is engaged along the proximal portion 1622 of the filter, the operator next advances a second sheath 1684 along the guidewire 14 until a second set of retrieval fingers 1686 engage a second notch 1688 form on the outer diameter of proximal portion 1622 proximal the first notch 1682. Once the second set of retrieval fingers 1686 engage the second notch 1688, a push tube 1668 is advanced along the guidewire 14, forcing the spring 1662 into compression, and causing the sleeve 1612 to radially expand and disengage from the guidewire 14, as shown in FIG. 37.

Figure 38:
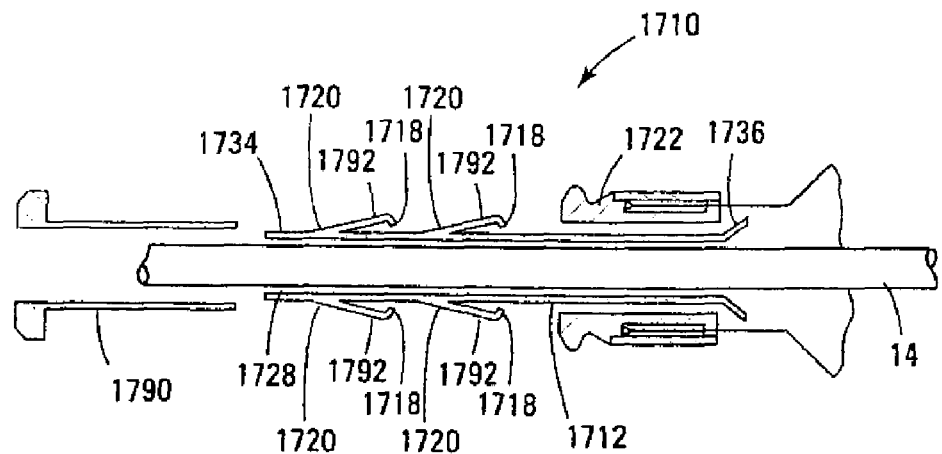
FIG. 38 is a cross-sectional view of an anchoring mechanism in accordance with another embodiment of the present invention, wherein the anchoring mechanism includes one or more latches.

FIG. 38 illustrates an anchoring mechanism 1710 in accordance with yet another exemplary embodiment of the present invention. Anchoring mechanism 1710 comprises a tubular member 1712 slidably and rotationally disposed a guidewire 14, a locking tube 1726, and a filter mount 1722. Tubular member 1712 has a proximal end 1734, a distal end 1736, and an inner lumen 1728 configured to receive the guidewire 14. The filter mount 1722, which forms the proximal portion of an embolic protection filter (not shown), is slidably and rotationally disposed about the tubular member 1712. The distal end 1736 of tubular member 1712 is flared slightly such that, in use, the filter mount 1722 is prevented from sliding off the distal end 1736 of the tubular member 1722. If desired, the filter mount 1722 may be formed of a radiopaque material such as stainless steel, gold or platinum to enable the operator to fluoroscopically judge the location of the device within the patient's body.

Tubular member 1712 further includes one or more latches 1792 adapted to frictionally engage the guidewire 14 when actuated. The latches 1792 may be formed by cutting the tubular member 1712 at various locations along its length and/or radius. The proximal end 1720 of each latch 1792 is attached to the tubular member 1712, and acts as a pivot to permit the latches 1792 to bend inwardly towards the guidewire 14. The distal end 1718 of each latch 1792, in turn, is bent at an angle of approximately 90°, forming a contact surface to frictionally engage the guidewire 14. A slight upward deflection is heat set into each latch 1792 to permit the tubular member 1712 to slide along the guidewire 14 when unconstrained radially.

A locking tube 1726 may be utilized to frictionally engage the one or more latches 1792 along the guidewire 14. Locking tube 1726 has an inner diameter slightly larger than the outer diameter of tubular member 1712, allowing the tube 1726 to slide over the tubular member 1712 to engage the one or more latches 1792.

Figure 39:
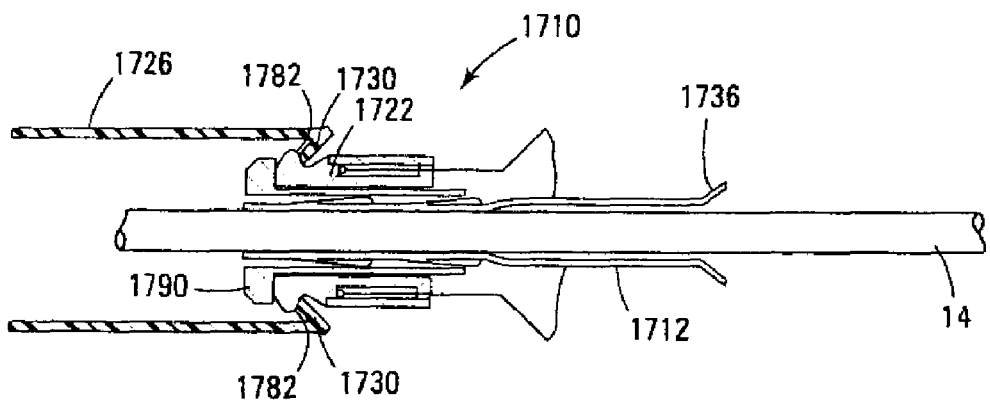
FIG. 39 is another cross-sectional view of the anchoring mechanism of FIG. 38, wherein a retrieval sheath is secured to the anchoring mechanism.

To frictionally engage the guidewire 14, the locking tube 1726 is advanced distally along the guidewire 14 to a location proximate and proximal the proximal end 1734 of tubular member 1712. Continued advancement of the locking tube 1726 distally forces the latches 1792 to rotate inwardly and frictionally engage the guidewire 14, as shown in FIG. 39.

Figure 40:
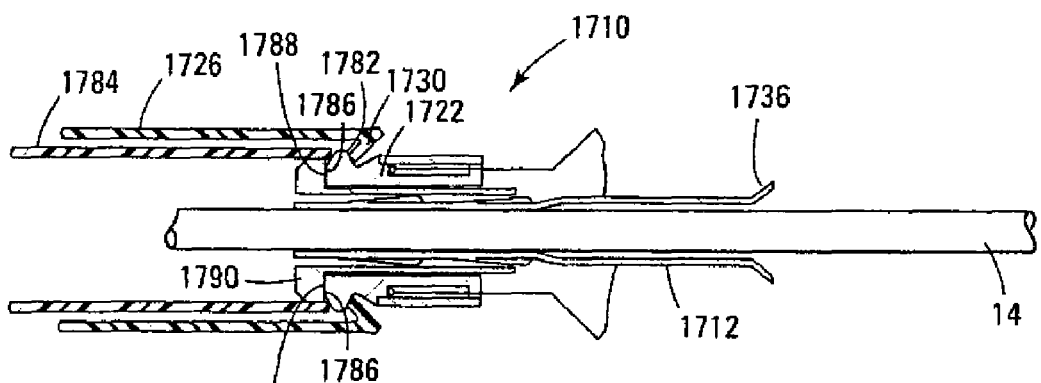
FIG. 40 is another cross-sectional view of the anchoring mechanism of FIG. 35, wherein a second sheath is advanced along the guidewire.

To subsequently disengage the latches 1792 from the guidewire 14, a retrieval system similar to that described with respect to FIGS. 35-37 may be employed. For example, as shown in FIG. 39, a retrieval sheath 1726 having one or more retrieval fingers 1730 may be advanced along the guidewire 14 and secured to the filter mount 1722 at a first notch 1782. Once engaged, a second sheath 1784 having a second set of retrieval fingers 1786 may be advanced along the guidewire 14 and locked onto a second notch 1788 formed on the locking tube 1726, as shown in FIG. 40. The second sheath 1784 can be retracted proximally until the one or more latches 1792 are unconstrained radially, allowing the tubular member 1712 to slide and rotate along the guidewire 14. The operator can then retract the second sheath 1784 proximally, causing the one or more latches 1792 to disengage from the guidewire 14.

FIG. 41 illustrates an anchoring mechanism 1810 in accordance with yet another exemplary embodiment of the present invention utilizing a wedge. Anchoring mechanism 1810 comprises an object 1812 that is slidably and rotationally disposed about a guidewire 14 in an unlocked position, and releasably secured to the guidewire 14 in a locked position. Object 1812 has a proximal section 1820 and a distal section 1818. The proximal section 1820 of object 1712 is configured to bend or flex inwardly towards the guidewire 14 when compressed radially by a wedge 1894.

In the exemplary embodiment illustrated in FIG. 41, object 1812 tapers distally, having a smaller outer diameter on proximal section 1820 than on the distal section 1818. One or more notches 1882 disposed within the outer surface of the object 1812 further permit the proximal section 1820 to bend or flex inwardly when wedge 1894 is advanced thereon.

The distal section 1818 of object 1812 may further optionally include a joint 1856 adapted to permit rotation of the object 1812 relative to the proximal portion 1822 of the embolic protection filter 1814. In use, joint 1856 permits rotation of the embolic protection filter 1814 within the vessel while substantially preventing movement of the anchoring mechanism 1810 along the guidewire 14.

To frictionally engage the object 1812 along the guidewire 14, a push tube 1868 can be advanced distally, forcing the wedge 1894 to slide along the object 1812. A sheath 1826 having a force-calibrated tab 1830 adapted to bend in only one direction in response to a sufficient force exerted thereon can be utilized to hold the object 1812 in place when advancing the wedge 1894. Continued movement of the wedge 1894 relative to the object 1812 causes the object 1812 to compress radially, forcing the proximal section 1820 to bend inwardly and frictionally engage the guidewire 14. Once engaged, the retrieval sheath 1826 can be withdrawn proximally until the force-calibrated tab 1830 bends and compresses against the wedge 1894, and until the embolic protection filter 1814 is deployed within the vessel, as shown in FIG. 42. The push tube 1868 can then be withdrawn proximally from the body, if desired.

In an alternative embodiment illustrated in FIGS. 43-45, an anchoring mechanism 1910 in accordance with the present invention may include an object 1912 that tapers proximally. As shown in FIG. 43, object 1912 has a larger outer diameter on the proximal section 1920 than on the distal section 1918. The proximal section 1920 is configured to bend or flex inwardly towards the guidewire 14 when compressed radially by a wedge 1994. One or more notches 1982 disposed within the outer surface of the object 1912 further permit the proximal section 1920 to bend or flex inwardly when wedge 1994 is advanced thereon.

In a first (unlocked) position illustrated in FIG. 43, object 1912 is slidably and rotationally disposed about the guidewire 14. To frictionally engage the object 1912 along the guidewire 14, a push tube 1968 is advanced distally against the object 1912, forcing the object 1912 to slide relative to the wedge 1994, as shown in FIG. 44. A sheath 1926 having a force-calibrated tab 1930 adapted to bend in only one direction in response to a sufficient force exerted thereon can be utilized to hold the wedge 1994 stationary when advancing the object 1912 via the push tube 1968. Continued advancement of the push tube 1968 distally, or in the alternative, retraction of the retrieval sheath 1926 proximally, causes the force-calibrated tab 1930 to bend and compress against the wedge 1994, as shown in FIG. 45.

Figure 46:
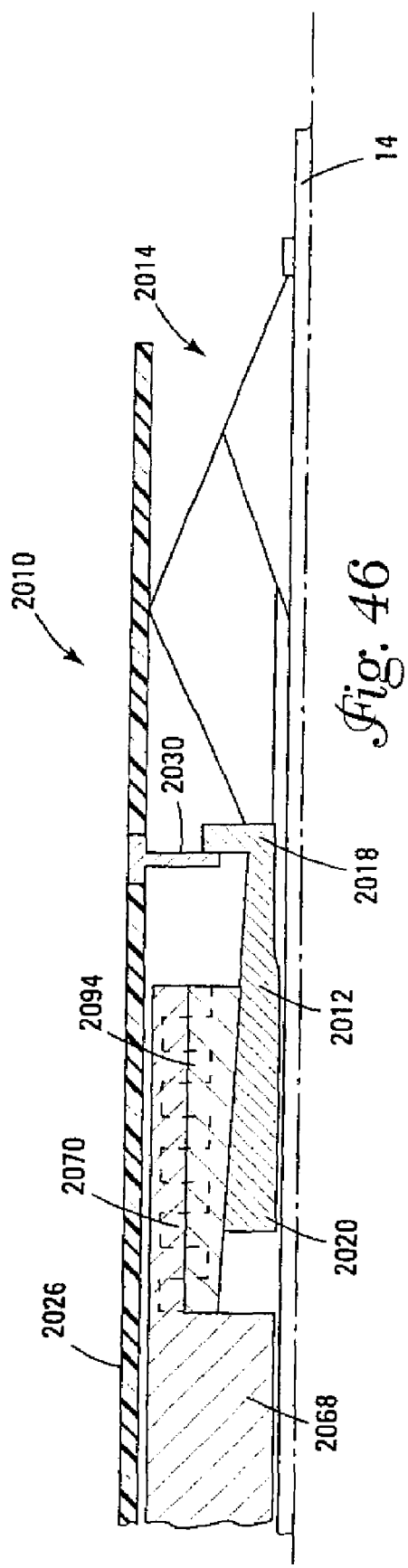
FIG. 46 is a cross-sectional view of an anchoring mechanism in accordance with another embodiment of the present invention employing a threaded wedge.
Figure 47:
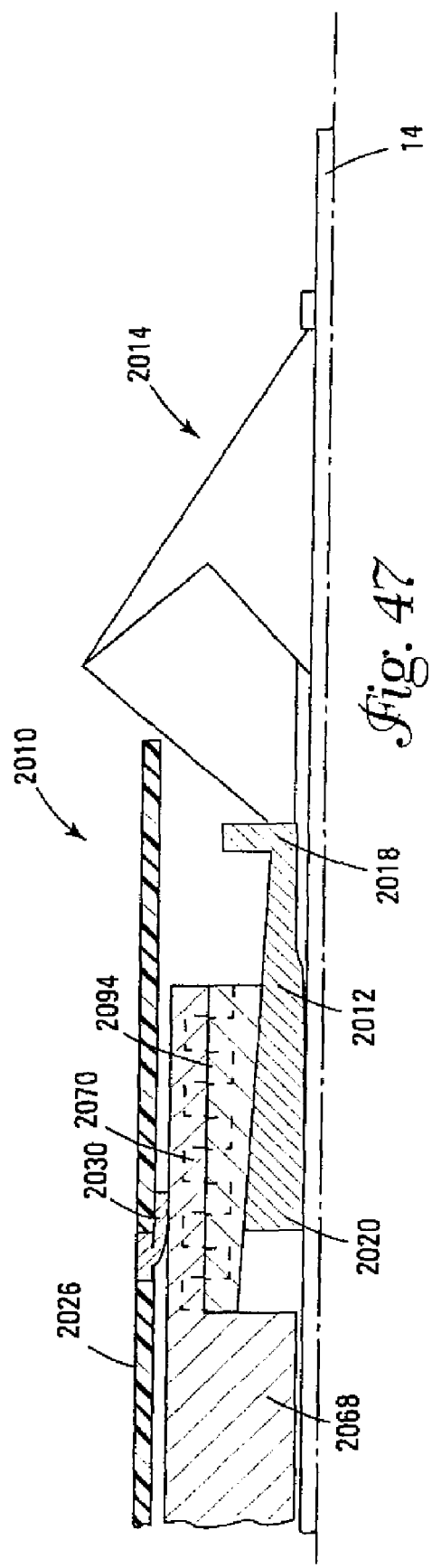
FIG. 47 is another cross-sectional view of the anchoring mechanism of FIG. 46, wherein the anchoring mechanism is releasably secured to the guidewire.

In an alternative embodiment illustrated in FIGS. 46-47, an anchoring mechanism 2010 in accordance with the present invention may include a push tube 2068 having threads configured to engage a corresponding set of threads disposed on the wedge 2094. Anchoring mechanism 2010 comprises an object 2012 having a proximal section 2020 and a distal section 2018, a retrieval sheath 2026, a wedge 2094, and a push tube 2068. The object 2012 tapers proximally, and forms the proximal portion of an embolic protection filter 2014. The proximal section 2020 of object 2012 is configured to bend or flex inwardly towards the guidewire 14 when compressed radially by the wedge 2094.

In the exemplary embodiment illustrated in FIGS. 46-47, wedge 2094 includes threads on its outer diameter configured to mate with a corresponding set of threads disposed on a reduced inner diameter distal portion 2070 of the push tube 2068.

To frictionally engage the object 2012 along the guidewire 14, push tube 2068 is retracted proximally, forcing the proximal section 2020 of the object 2012 to bend inwardly and frictionally engage the guidewire 14. Once engaged, the retrieval sheath 2026 may be withdrawn proximally, causing the force-calibrated tab 2030 to bend and compress against the wedge 2094, as shown in FIG. 47.

Figure 48:
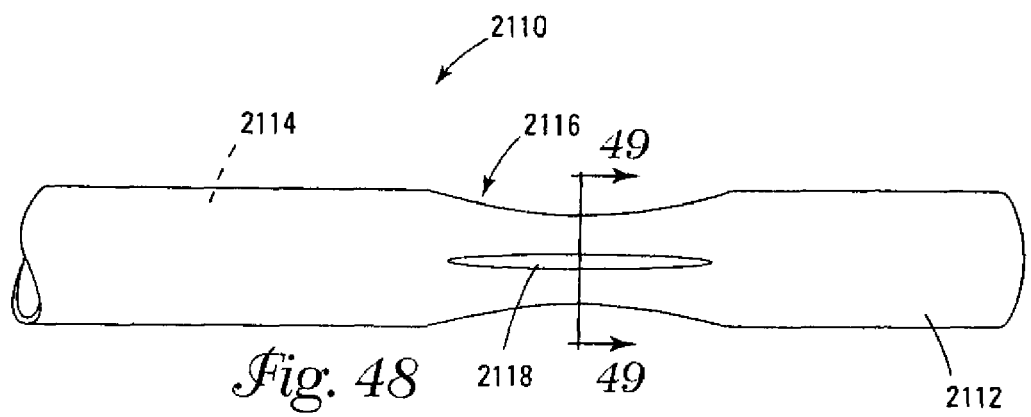
FIG. 48 is a perspective view of an anchoring mechanism in accordance with another embodiment of the present invention, wherein the anchoring mechanism includes a slotted tube.

FIG. 48 illustrates an anchoring mechanism 2110 in accordance with yet another exemplary embodiment of the present invention utilizing a slotted tube. As shown in FIG. 48, anchoring mechanism 2110 comprises a slotted tube 2112 having an inner lumen 2114 configured to slidably receive a guidewire (not shown). As with any of the previous embodiments, the slotted tube 2112 may form the proximal portion of an embolic protection filter, or may act as a proximal stop to prevent proximal movement of the filter along the guidewire.

Figure 49:
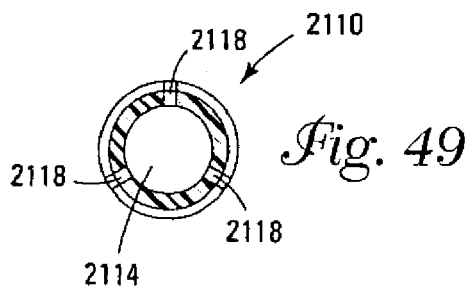
FIG. 49 is a cross-sectional view of the anchoring mechanism of FIG. 48 along line 49-49.

In the exemplary embodiment illustrated in FIG. 48, slotted tube 2112 comprises a thin-wall tube formed from a shape-memory material such as Nitinol. Slotted tube 2112 includes a necked-down portion 2116 having an inner diameter that is slightly smaller than the outer diameter of the guidewire. Several slots 2118 located within the necked-down portion 2116 are configured to expand slightly to allow the guidewire to slide within lumen 2114 when the slotted tube 2112 is unconstrained radially. As can be seen in greater detail in FIG. 49, the slots 2118 are circumferentially disposed 120° apart from each other, and extend through the wall of the slotted tube 2112.

Figure 50:
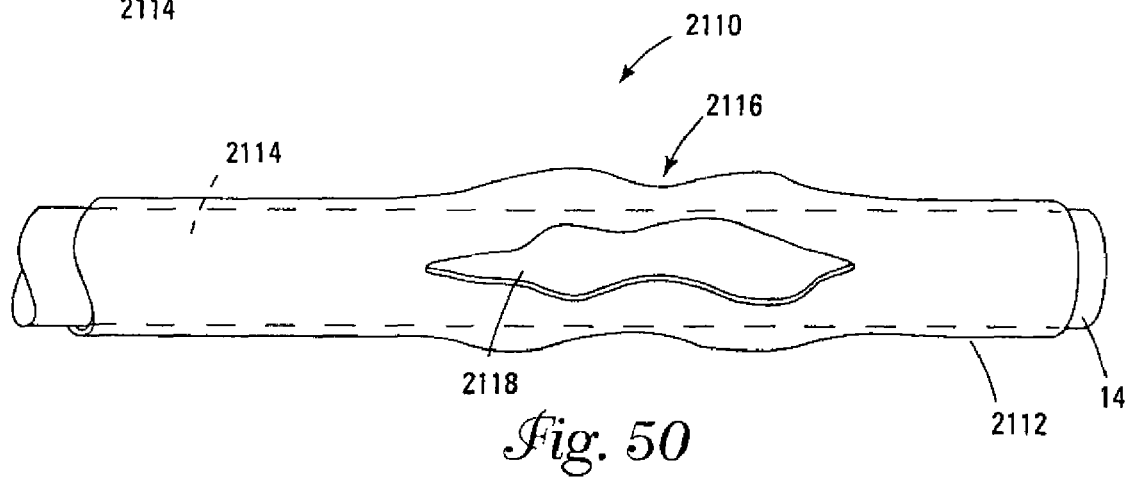
FIG. 50 is another perspective view of the anchoring mechanism of FIG. 48, wherein the anchoring mechanism is shown slidably disposed along a guidewire after heat setting.

To expand the slots 2116 in an outward direction, the slotted tube 2112 can be heat treated at an appropriate temperature using, for example, a heater or a laser. Once heated, the slots 2118 deform slightly, allowing the guidewire 14 to be inserted through the slotted tube 2112, as shown in FIG. 50. To facilitate heat setting of the slots 2116, a shape memory material such as Nitinol can be used. In an alternative implementation, the slots 2118 can be formed using an annealed steel or polymeric material. For example, the slots 2116 can be molded to a particular dimension using a polymeric material such as polytetraflouroethylene, polyvinylchloride or ABS plastic.

To engage the anchoring mechanism 2110 along the guidewire 14, a locking tube 2120 is advanced along the guidewire 14 to a point proximate and proximal the necked-down portion 2116 of slotted tube 2112. The locking tube 2120 has an inner diameter that is slightly larger than the outer diameter of the slotted tube 2112, allowing the locking tube 2120 to be advanced over the slotted tube 2112. To releasably secure the slotted tube 2112 to the guidewire 14, the operator continues to advance the locking tube 2120 distally until the necked-down portion 2116 compresses against the guidewire 14, as shown in FIG. 51.

Figure 52:
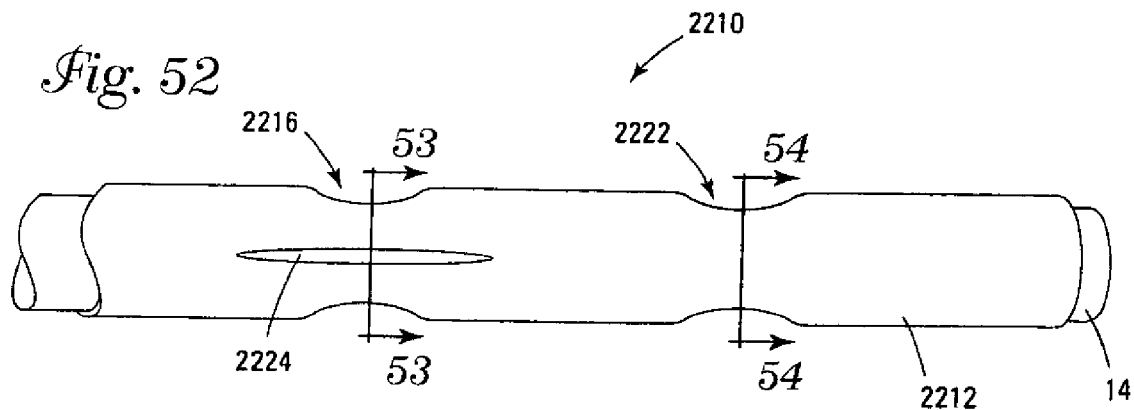
FIG. 52 is a perspective view of an anchoring mechanism in accordance with another embodiment of the present invention, wherein the anchoring mechanism includes a slotted tube having multiple necked-down regions.
Figure 53:
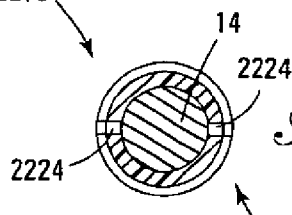
FIG. 53 is a cross-sectional view of the anchoring mechanism of FIG. 52 along line 53-53, showing the first necked-down portion.
Figure 54:
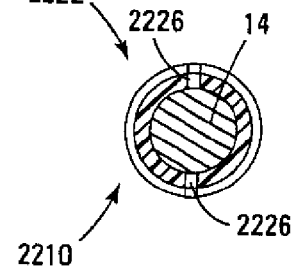
FIG. 54 is a cross-sectional view of the anchoring mechanism of FIG. 52 along line 54-54, showing the second necked-down portion.
Figure 55:
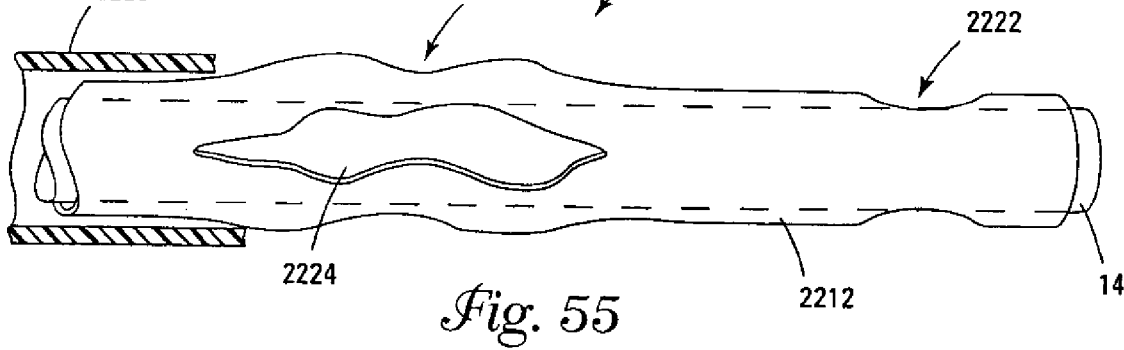
FIG. 55 is another perspective view of the anchoring mechanism of FIG. 52, wherein the anchoring mechanism is slidably disposed along the guidewire.

In an alternative embodiment illustrated in FIGS. 52-56, the slotted tube may include several necked down regions located along its length configured to releasably secure to the guidewire 14. As shown in FIG. 52, anchoring mechanism 2210 comprises a slotted tube having a first necked-down region 2216, and a second necked-down region 2220 located distal the first necked-down region 2216. The first necked-down region 2216 includes two slots 2224 circumferentially disposed 180° apart from each other, and that extend through the wall of the slotted tube 2212, as shown in FIG. 53. The second necked-down region 2222, in turn, includes two slots 2226 that are radially offset 90° from the slots 2224 on the first necked-down region 2216, as shown in FIG. 54.

Figure 51:
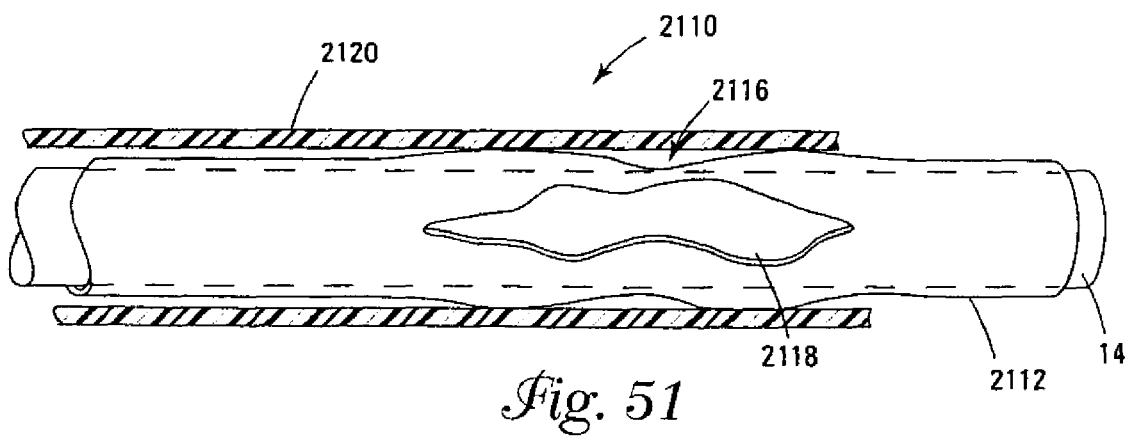
FIG. 51 is another perspective view of the anchoring mechanism of FIG. 48, wherein the anchoring mechanism is releasably secured to the guidewire.
Figure 56:
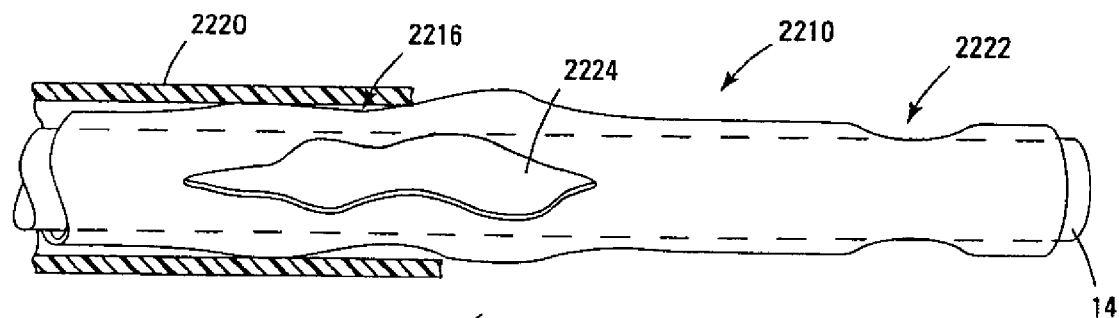
FIG. 56 is another perspective view of the anchoring mechanism of FIG. 52, wherein the anchoring mechanism is releasably secured to the guidewire.

To engage the anchoring mechanism 2210 along the guidewire 14, a locking tube 2220 similar to that discussed with respect to FIG. 51 is advanced along the guidewire 14 to a point proximate and proximal to the first necked-down portion 2216 of slotted tube 2212, as shown in FIG. 56. Continued advancement of the locking tube 2220 about the first necked-down portion 2216 compresses the slotted tube 2212 against the guidewire 14, as shown in FIG. 51. Further advancement of the locking tube 2220 distally causes the second necked-down portion 2222 to compress against the guidewire 14 in a similar manner.

Although the exemplary embodiment illustrated in FIGS. 52-56 illustrates two locking portions 2216, 2222 along the length of the slotted tube 2212, it is to be understood that other configurations are possible without deviating from the scope of the invention. For example, a slotted tube having three or more necked-down regions can be employed. Moreover, the number of slots (e.g. 4, 5, 6, etc.) disposed within each necked-down region can be increased, if desired, to provide a greater number of locations for the slotted tube to frictionally engage the guidewire.

To further increase the frictional force exerted on the guidewire, the inner diameter of the slotted tube may include a roughened surface. The roughened surface may be formed by welding several small beads to the inner surface, sand blasting the inner surface, or by machining small grooves into the inner surface of the slotted tube. The slotted tube may also be formed from a material having a relatively porous surface, thereby increasing the roughness of the surface.

In another alternative embodiment illustrated in FIGS. 57-59, an anchoring mechanism 2310 in accordance with the present invention may include a slotted tube 2312 comprising one or more portions 2328 having a relatively large section modulus, and one or more portions 2330 having a relatively small section modulus. As shown in a pre-heat treated position in FIG. 57, the slotted tube 2312 may include several circumferentially disposed slots 2332 extending through the wall of the slotted tube 2312. The one or more portions 2328 having a relatively large section modulus are configured to distribute the axial force applied to the slotted tube when the embolic protection filter is moved along the guidewire 14. In use, the slots 2332 formed about the slotted tube 2312 are configured to expand slightly to allow the guidewire 14 to slide and rotate within the slotted tube 2312 when unconstrained radially.

As can be seen in FIG. 58, the slots 2332 may be formed in a direction substantially parallel to centerline of the slotted tube. The slots 2332 may be heat treated as discussed with respect to the previous embodiment, or may be formed during manufacture. Although the slots 2332 illustrated in FIG. 58 are disposed along a line substantially parallel to the centerline of the slotted tube 2312, other configurations are possible. In one embodiment, for example, the one or more slots may be helically disposed about the slotted tube 2312.

To engage the anchoring mechanism 2310 along the guidewire 14, a locking tube 2320 can be advanced along the guidewire 14 to a point proximate and proximal to the necked-down portion 2316 of slotted tube 2312. Continued advancement of the locking tube 2312 distally about the necked-down portion 2316 compresses the slotted tube 2312 against the guidewire 14, as shown in FIG. 59. Several protrusions 2334 disposed on the outer diameter of the slotted tube 2312 are configured to frictionally engage the locking tube 2320 against the slotted tube 2312.

Having thus described the several embodiments of the present invention, those of skill in the art will readily appreciate that other embodiments may be made and used which fall within the scope of the claims attached hereto. Numerous advantages of the invention covered by this document have been set forth in the foregoing description. Changes may be made in details, particular in matters of shape, size and arrangement of parts without exceeding the scope of the invention. For example, while several of the embodiments illustrated herein illustrate the attachment of an embolic pro- tection filter to the guidewire, it is to be understood that other intravascular devices may employ the anchoring mechanisms discussed herein. It will be understood that this disclosure is, in many respects, only illustrative.

What is claimed is:

1. An intravascular device comprising:
   an embolic protection filter slidably disposed on a guidewire;
   anchoring means for attaching the embolic protection filter to the guidewire at a position not predetermined by components of the anchoring means attached to the guidewire, said anchoring means comprising an object actuatable between an unlocked position and a locked position, wherein the anchoring means is slidably disposed along the guidewire in the unlocked position, is releasably secured to the guidewire in the locked position, and has a portion attached to the embolic filter; and
   placement means for actuating said anchoring means between the unlocked position and locked position;
   wherein the anchoring means is self-biased toward the guidewire;
   wherein the placement means may be removed from the guidewire after actuating the object into the locked position.

2. An intravascular device comprising:
   an embolic protection filter slidably disposed on a guidewire;
   anchoring means for attaching the embolic protection filter to the guidewire at a position not predetermined by components of the anchoring means attached to the guidewire, said anchoring means comprising an object actuatable between an unlocked position and a locked position, wherein the anchoring means is slidably disposed along the guidewire in the unlocked position, is releasable secured to the guidewire in the locked position, and has a portion attached to the embolic filter; and
   placement means for actuating said anchoring means between the unlocked position and locked position;
   wherein the anchoring means is self-biased toward the guidewire;
   wherein the placement means may be advanced over the guidewire when the object is in the locked position.

3. The intravascular device of claim 1 or 2, wherein the anchoring means comprises at least one radial projection extending from the embolic protection filter, said radial projection having a first position in which it is not in contact with the guidewire and a second position in which it is in frictional engagement with the guidewire.

4. The intravascular device of claim 3,
   wherein the radial projection is actuatable between the first position and the second position.

5. The intravascular device of claim 4, wherein the radial projection is actuatable between the first position and the second position by moving the placement means from a first position to a second position.

6. The intravascular device of claim 3,
   wherein the radial projection is actuatable between the second position and the first position.

7. The intravascular device of claim 6, wherein the radial projection is actuatable between the second position and the first position by moving the placement means from a second position to a first position.

* * * * *